United States Patent [19]
Dombrowski, Jr. et al.

[11] Patent Number: 5,196,297
[45] Date of Patent: Mar. 23, 1993

[54] RECORDING MATERIAL AND PROCESS OF USING

[75] Inventors: Edward J. Dombrowski, Jr., Allston; James R. Freedman, Newton Centre; Patrick F. King, North Quincy, all of Mass.

[73] Assignee: Polaroid Corporation, Cambridge, Mass.

[21] Appl. No.: 935,534

[22] Filed: Dec. 5, 1986

Related U.S. Application Data

[63] Continuation-in-part of Ser. No. 809,157, Dec. 16, 1985, abandoned.

[51] Int. Cl.$^5$ .................... G03C 1/73; G03C 1/494; B41M 5/30; B41M 5/34
[52] U.S. Cl. .................... 430/338; 430/332; 430/341; 430/342; 430/343; 430/346; 430/348; 430/350; 430/363; 430/944; 430/964; 430/618; 430/619; 430/620; 503/201; 503/204; 503/218; 503/220; 503/221; 503/224; 503/226
[58] Field of Search .............. 430/332, 338, 341, 363, 430/944, 964, 342, 343, 346, 348, 350, 618, 619, 620; 503/218, 220, 221, 224, 201, 204, 226

[56] References Cited

U.S. PATENT DOCUMENTS

| | | |
|---|---|---|
| 2,097,435 | 11/1937 | Austin et al. |
| 3,489,900 | 4/1970 | Tewksbury et al. |
| 3,924,027 | 12/1975 | Toranosuke et al. |
| 4,020,232 | 4/1977 | Kohmura et al. ............ 503/218 |
| 4,021,240 | 5/1977 | Cerquone et al. |
| 4,122,089 | 10/1978 | Kimura et al. ............ 503/221 |
| 4,132,436 | 1/1979 | Ishige et al. |
| 4,133,933 | 1/1979 | Sekine et al. |
| 4,390,616 | 6/1983 | Sato et al. ............ 430/338 |
| 4,452,883 | 6/1984 | Frenchik et al. |
| 4,460,681 | 7/1984 | Frenchik. |
| 4,502,067 | 2/1985 | Matsuda et al. |
| 4,720,449 | 1/1988 | Borror et al. ............ 430/338 |
| 4,904,572 | 2/1990 | Dombrowski, Jr. et al. ........ 430/332 |

FOREIGN PATENT DOCUMENTS 1417382  7/1975  United Kingdom.

OTHER PUBLICATIONS

March et al., Textbook "Advanced Organic Chemistry", McGraw-Hill, Inc., 1977, p. 349.
Merck et al., The Merck Index, 1976, Merck & Co., Inc. Rahway, N.J., p. 941.
Ernst et al., C.A. vol. 83, 1975, 83:163837f, p. 516.
Gilman, Henry, Org. Chem. An Advanced Treatise, vol. III, John Wiley and Sons, N.Y. 1953, pp. 247–255.
R. Meyer, Ber. 33, pp. 2570–2583, (and translation).
Soloveichik et al., Zhurnal Org. Khi., vol. 10, No. 3., pp. 611–615, Mar. 1974 (translation only).
O'Brochta et al., J. Am. Chem. Soc., 61, pp. 2765–2768 (1939).
Stadler, P. A., Helvitica Chimica Acta, vol. 61, Fasc. 5 (1978), No. 162, p. 1675 (and translation).
Chandrasekaran et al., Synthetic Communications, 12(9), pp. 727–731 (1982).
Kaloustian, et al., Tetrahedron Letters, vol. 22, pp. 413–416 (1981).
Carpenter, J. W. and Lauf, P. W., "Photothermographic Silver Halide Systems", Research Disclosure No. 17029 (Jun. 1978).

*Primary Examiner*—Charles L. Bowers, Jr.
*Attorney, Agent, or Firm*—Stanley H. Mervis

[57] ABSTRACT

This invention relates to novel recording materials which employ color-forming di- and triarylmethane compounds possessing certain S-containing ring-closing moieties, namely, or thiolactone, dithiolactone or thioether ring-closing moiety and to a method of forming color by contacting these dye precursor compounds with a Lewis acid material capable of opening the thiolactone, dithiolactone or thioether ring-closing moiety whereby the compound is rendered colored, that is, converted to its chromophore color.

45 Claims, No Drawings

RECORDING MATERIAL AND PROCESS OF USING

CROSS-REFERENCE TO RELATED APPLICATIONS

This application is a continuation-in-part of copending U.S. patent application Ser. No. 809,157 filed Dec. 16, 1985, now abandoned.

BACKGROUND OF THE INVENTION

1. Field of the Invention

This invention relates to recording materials, particularly thermographic and photothermographic image-recording materials employing certain di- and triarylmethane dye precursor compounds and to a method of forming color employing the dye precursor compounds.

2. Background Art

Various dry image-recording materials that can be processed by a dry method only, that is, without the use of any treatment with liquids have been proposed. Among such image-recording materials are the thermographic and photothermographic materials of the silver salt type which employ moderate heating to develop a visible image and which comprise an oxidation-reduction image-forming combination comprising a non-photosensitive organic silver salt oxidizing agent such as the silver salt of a long chain fatty acid and a reducing agent for silver ions, typically, an organic reducing agent. In addition to the above, the photothermographic materials also include a photosensitive compound such as a light-sensitive silver halide or a photosensitive compound-forming component such as a component capable of forming a light-sensitive silver halide. The latter materials are often referred to as heat developable photographic materials and require an imagewise exposure to light to form a latent image prior to the heat development step.

The addition of dye-forming compounds to materials of the silver salt type for providing a color image or a color enhanced image also has been proposed. Usually color formation is achieved by color coupling to form a dye image, for example, by including a color-forming coupler and using a p-phenylenediamine, sulfonamidophenol or other color-developing agent as the organic reducing agent or by oxidation of a leuco dye to its colored form, for example, by employing a readily oxidizable indoaniline or phenolic leuco dye as the organic reducing agent. These and other means for generating dye images in silver salt materials have been described by J. W. Carpenter and P. W. Lauf in their review of "Photothermographic Silver Halide Systems", Research Disclosure, No. 17029, June, 1978. The formation of multicolor images using at least 2 or 3 color image-forming layers also has been disclosed in U.S. Pat. Nos. 4,021,240, 4,452,883 and 4,460,681.

Other dry image-recording materials for producing color images from colorless precursor(s) also have been proposed. One system commonly employed for pressure-sensitive and heat-sensitive recording materials to produce dye images comprises a two-component system utilizing a coloration reaction between a colorless dye precursor (color former) and an acidic material (color developer). Among the colorless dye precursors used as the color former are triarylmethane compounds including bridged triarylmethane compounds possessing a lactone, lactam or other ring-closing moiety, for example, 3,3-bis(p-dimethylaminophenyl)-6-dimethylaminophthalide (Crystal Violet Lactone), 3-piperidino-6-methyl-7-anilinofluoran and Rhodamine B anilinolactam. The acidic material used as the color developer is usually a phenol derivative or an aromatic carboxylic acid derivative, for example, p-tert-butylphenol, 2,2-bis(p-hydroxyphenyl) propane, o-hydroxynaphthoic acid, p-hydroxybenzoic acid, 3,5-di-tert-butylsalicylic acid and so forth.

In these two-component systems, the color former and the color developer can be carried on the same or on separate supports. Where the two components are coated on the same side of a common support, a binder or some other means such as encapsulation is employed for physically separating the color former and color developer to prevent premature mixing and coloration. Images are formed by the imagewise application of pressure, heat, electricity or other stimulus to effect contact between the two components to bring about the coloration reaction. Depending upon the dye precursor used as the color former, the coloration reaction brought about by contacting the two components may comprise dissociation, or it may comprise ring-opening in those compounds containing a cyclic ring-closing moiety as part of their structure. For example, color formers such as the aforementioned triarylmethane compounds possessing a lactone or lactam moiety ring-closed on the methane carbon atom become ring-opened and colored by an ionization or hydrogen-bonding reaction when contacted with the acidic material. Such imaging systems for pressure-sensitive, heat-sensitive and electrothermic recording materials are described in U.S. Pat. Nos. 3,924,027, 4,502,067, 4,133,933 and in U.S. Pat. No. 4,132,436.

Although 3,3-disubstituted thiophthalides and dithiophthalides have been disclosed previously, none of the triarylmethane compounds described are dye precursors, i.e., color formers, since they do not exhibit the color-forming properties of dyes. In particular, R. Meyer, Ber. 33, pp. 2570-2576 and R. Meyer and J. Szanecki, ibid, pp. 2577-2583 disclose the synthesis of 3.3-dithiotluorane, dithiophenylphthalide (3,3-diphenylthiophthalide) and dithiodichlorofluorane by fusing the corresponding phthalides with phosphorus pentasulfide. The 3.3-dithiofluorane and the dithiodiphenylphthalide lack the auxochromic substituents necessary to complete the auxochromophoric system of a triarylmethane dye. The dithiodichlorofluorane also does not exhibit the properties of a dye, presumably because the chloro groups are not providing an auxochromic effect.

I. P. Soloveichik, et al., Zhurnal Organicheskoi Khimii, Vol. 10, No. 3, pp. 615-618, March, 1974 disclose the preparation of 3,3-diphenylthiophthalide by reacting the 3,3-diphenyldithiophthalide of Meyer and Szanecki with mercuric acetate and also by reacting o-benzoylbenzoic acid and phosphorus pentasulfide followed by phenylation with the Friedel-Crafts reaction as previously described by I. O'Brochta, et al., J. Am. Chem. Soc., 61, 2762 (1959). U.S. Pat. No. 2,097,435 discloses a synthesis for thiophthalides including 3,3-diphenylthiophthalide by reacting the corresponding phthalide with sodium hydrosulfide under anhydrous conditions in the absence of air or oxygen. Like the 3,3-diphenyldithiophthalide discussed above, 3,3-diphenylthiophthalide is not a dye precursor since the 3,3-phenyl moieties lack an auxochromic substituent to impart dye properties.

As discussed in Gilman, Henry, Organic Chemistry, An Advanced Treatise, Vol. III, John Wiley & Sons, New York, 1953, pp. 247-55, a chromophore called a chromogene may be colored but does not yet represent a dye. To achieve this a further introduction of salt-forming groups, "auxochromes", into the molecule is required. The function of chromophore and auxochrome groups according to modern theory is necessary for modifying the molecule so as to introduce the possibility of resonance and thus color.

SUMMARY OF THE INVENTION

The present invention is concerned with novel imaging systems useful for heat-sensitive, light-sensitive, pressure-sensitive and other image-recording materials for producing dye images that employ di- and triarylmethane dye precursor compounds possessing certain S-containing ring-closing moieties, namely, a thiolactone, dithiolactone or thioether moiety. When contacted with a Lewis acid material capable of opening the thiolactone, dithiolactone or thioether moiety, the compound is rendered colored, i.e., converted to its chromophore color which is a function of the auxochromophoric system of the di- or triarylmethane dye. Indeed, the ability of these dye precursor compounds to form a colored dye almost instantaneously when contacted with Ag+ renders these compounds eminently suitable for use as color formers in reactions employing silver salts including imaging systems employing inorganic silver salts, such as, silver halides and particularly imaging systems employing organic silver salts, such as silver behenate. In systems of the latter type, color formation is particularly efficient since it is effected by a phase change, i.e., effected by melting of the organic silver salt to provide the Ag+ necessary for coloration rather than requiring a change of state.

Besides their ability to readily form color with Lewis acids and especially with Ag+, these dye precursor compounds possess other properties that compare favorably with color formers previously used in heat-, light- and pressure-sensitive recording materials. They are substantially colorless at the concentrations used in the image-recording layers and are relatively free from decomposition or coloration due to heat, light, humidity, etc. during storage, that is, prior to contacting with the Lewis acid. They provide a wide range of colors as may be desired not only for monochromes and bichromes but for full color images, and the color images formed exhibit reasonable resistance to heat, light and humidity. Moreover, when they are employed in imaging systems which use heat to form or develop color, color formation may be readily achieved at only moderately elevated temperatures.

It is, therefore, one object of the present invention to provide a method of forming color employing certain di- and triarylmethane dye precursor compounds.

It is another object of the present invention to provide novel recording materials employing said compounds.

Other objects of the invention will in part be obvious and will in part appear hereinafter.

The invention accordingly comprises the method involving the several steps and the relation and order of one or more of such steps with respect to each of the others, and the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DESCRIPTION OF THE PREFERRED EMBODIMENTS

As noted above, the present invention is concerned with novel recording materials employing color-forming di- and triarylmethane compounds possessing certain S-containing ring-closing moieties and with color formation employing these compounds. Specifically, the method of forming color according to the present invention comprises contacting (a) a di- or triarylmethane dye precursor compound possessing within its di- or triarylmethane structure an aryl group substituted in the ortho position to the meso carbon atom with an S-containing moiety ring-closed on the meso carbon atom selected from a thiolactone, dithiolactone or thioether moiety and (b) a Lewis acid material capable of opening the thiolactone, dithiolactone or thioether moiety whereby said compound is rendered colored, i.e., converted to its chromophore color which is a function of the auxochromophoric system of the triarylmethane dye.

The Lewis acid material may be an organic or inorganic electron pair acceptor, and such materials suitable for a given thiolactone, dithiolactone or thioether dye precursor may be determined empirically. In this regard, it will be understood that the thiolactone, dithiolactone and thioether dye precursors do not react with all Lewis acids but that each thiolactone, dithiolactone and thioether reacts with at least one Lewis acid. Where both sulfur and oxygen are present in the ring-closed moiety as in the thiolactones, Lewis acid materials such as boron trifluoride etherate and aluminum chloride may be employed, but preferably, the Lewis acid material selected for both the thiolactones and dithiolactones and for the thioethers has a strong preference for coordinating with sulfur such as the metal ions classified as "soft acids" by Pearson, Ralph G., Hard and Soft Acids and Bases, Chem. Brit., 1967, 3, (3), p. 103. Preferably, the metal ion is that of a heavy metal, such as silver, gold, mercury and palladium. Silver is particularly preferred because of its exceptional ability for complexing with the thiolactone, dithiolactone and thioether moieties.

Contacting the dye precursor and Lewis acid material may be achieved in any suitable and convenient manner as desired for a given color-forming application, for example, by admixing solutions of the two components or by applying the Lewis acid material in liquid, gaseous, melted or other fluid form to the dye precursor coated on or absorbed into a substrate. Also, color formation may be effected imagewise. As an illustration, the dye precursor may be disposed in a layer and a solution of the Lewis acid material applied imagewise by coating through a stencil, spraying in an imagewise pattern, etc. or a Lewis acid material such as Ag+ may be provided imagewise as a function of processing a selectively exposed photosensitive silver halide layer adjacent the dye precursor layer by applying an aqueous processing composition.

Rather than applying a solution, the Lewis acid material and dye precursor may be used in "dry" systems. They may be used as solids or one or both may be encapsulated and contained in a single sheet in the same or different layers or contained in separate superposed sheets, and color formation brought about in an imagewise fashion by the imagewise application of heat, pressure or other stimulus necessary to effect imagewise contact between the two components. In systems employing two sheets, the dye precursor may be coated in a binder on one sheet and the Lewis acid material coated in a binder on the other and heat applied imagewise to the superposed sheets to effect melting and contact of the two components, or a sheet coated with a layer of dye precursor encapsulated in oil may be superposed with the second sheet coated with Lewis acid material, and pressure applied imagewise to the superposed sheets to rupture the capsule walls and effect contact between the two components.

In a preferred embodiment, the two components are contained in the same sheet, that is, a single support carries the dye precursor and the Lewis acid material. The Lewis acid material preferably is a silver salt. In a particularly preferred embodiment, a thermographic image-recording material for producing dye images is provided which comprises a support carrying a di- or triarylmethane thiolactone, dithiolactone or thioether dye precursor, an organic silver salt and optionally, a heat-fusible organic acidic material. For photothermographic use, the image-recording material additionally includes in catalytic association with the organic silver salt, a photosensitive silver halide or a photosensitive silver halide-forming component and a reducing agent. Preferably, the dye precursor is a triarylmethane thiolactone, particularly a thiophthalide and the organic silver salt is silver behenate.

Novel di- and triarylmethane dye precursors particularly useful in the imaging systems in accordance with this invention are disclosed and claimed in the copending application of P. F. King Ser. No. 935,533 filed Dec. 5, 1986, now abandoned which is a continuation-in-part of application Ser. No. 809,157 filed Dec. 16, 1985.

The novel di- and triarylmethane dye precursors useful in the present invention may be represented by the formula

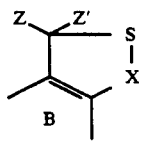 (I)

wherein X is

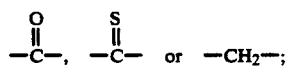

ring B represents a substituted or unsubstituted carbocyclic aryl ring, e.g., of the benzene or naphthalene series or a heterocyclic aryl ring, e.g., pyridine or pyrimidine; and Z and Z' taken individually represent the moieties, to complete the auxochromophoric system of a diarylmethane or a triarylmethane dye when said S-containing ring is open and Z and Z' when taken together represent the bridged moieties to complete the auxochromophoric system of a bridged triarylmethane dye when said S-containing ring is open. In a preferred embodiment, B represents a substituted or unsubstituted benzene ring and Z and Z' taken individually represent the aryl moieties, the same or different, to complete the auxochromophoric system of a triarylmethane dye when said S-containing ring is open and Z and Z' when taken together represent the bridged aryl moieties to complete the auxochromophoric system of a briged triarylmethane dye when said S-containing ring is open. Usually, at least one of Z and Z' whether taken individually or together possesses as an auxochromic substituent, a nitrogen, oxygen or sulfur atom or a group of atoms containing nitrogen, oxygen or sulfur. Preferably, X is

In the triarylmethane compounds represented in formula I above, the aryl moieties Z and Z', when taken individually, may be the same or different and typically represent heterocyclic aryl groups containing nitrogen, oxygen or sulfur as the heterocyclic atom, particularly N-heterocyclic aryl groups such as julolidin-3-yl, indol-3-yl, pyrr-2-yl, carbazol-3-yl, and indolin-5-yl wherein the N atom of the indolyl, pyrryl, carbazolyl and indolinyl groups may be substituted with hydrogen or alkyl having 1 to 6 carbon atoms, or the aryl moieties Z and Z' typically may be carbocyclic aryl, particularly phenyl or naphthyl groups which include an appropriately positioned auxochromic substituent, i.e., an atom or group that produces an auxochromic effect, which substituent is usually positioned para to the meso carbon atom. Typically, Z and Z' when taken together represent aryl groups bridged by a heteroatom, such as, oxygen, sulfur or nitrogen to form, for example, 4H-chromeno [2,3-C] pyrazole and particularly represent carbocyclic aryl groups, such as, phenyl groups bridged with a heteroatom, preferably oxygen, sulfur or nitrogen substituted with hydrogen or an alkyl group having 1 to 6 carbon atoms to provide a xanthene, thioxanthene or an acridine dye, which dyes possess an auxochromic substituent(s) para to the meso carbon atom, i.e., in the 3-position or in the 3,6-positions or meta and para to the meso carbon atom, i.e., in the 3,7-positions.

In the diarylmethane compounds, one of Z and Z' may be heterocyclic aryl or carbocyclic aryl as discussed, above and the other of Z and Z' may be, for example, phenoxy, thiophenoxy, alkoxy containing 1 to 20 carbon atoms, alkylthio containing 1 to 20 carbon atoms, -N,N-(disubstituted)amino wherein each said substituent may be alkyl containing 1 to 20 carbon atoms, carbocyclic aryl containing 6 to 12 carbon atoms, aralkyl containing 7 to 15 carbon atoms particularly phenyl- and naphthyl-substituted alkyl or alkaryl containing 7 to 15 carbon atoms particularly alkyl-substituted phenyl and naphthyl. Representative alkyl groups include methyl, butyl, hexyl and octadecyl and representative aryl groups include phenyl and naphthyl. Representative alkaryl groups include p-octylphenyl, o-methylnaphthyl and p-hexylphenyl, and representative aralkyl groups include phenethyl, benzyl and naphthylmethyl.

Examples of useful auxochromic substituents include —$OR_1$ wherein $R_1$ is hydrogen, alkyl usually having 1 to 6 carbon atoms, aralkyl usually having 7 to 15 carbon atoms, alkaryl usually having 7 to 15 carbon atoms or carbocyclic aryl usually having 6 to 12 carbon atoms; —$SR_2$ wherein $R_2$ has the same meaning given for $R_1$; —$NR_3R_4$ wherein $R_3$ and $R_4$ each represent hydrogen, alkyl usually having 1 to 6 carbon atoms, $\beta$-substituted ethyl, cycloalkyl usually having 5 to 7 carbon atoms, aralkyl usually having 7 to 15 carbon atoms, alkaryl usually having 7 to 15 carbon atoms or

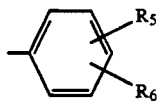

wherein $R_5$ and $R_6$ each are hydrogen, alkyl usually having 1 to 6 carbon atoms, halo such as chloro, bromo, fluoro and iodo, nitro, cyano, alkoxycarbonyl wherein said alkoxy has 1 to 6 carbon atoms, sulfonamido (—NHSO$_2$R$_0$), sulfamoyl (—SO$_2$NHR$_0$), sulfonyl (—SO$_2$R$_0$), acyl (—COR$_0$) or carbamyl (—CONR$_0$) wherein $R_0$ usually is alkyl having 1 to 20 carbon atoms, benzyl or phenyl and $R_3$ and $R_4$ taken together represent the atoms necessary to complete a heterocyclic ring usually piperidino, pyrrolidino, N-methylpiperidino, morpholino or

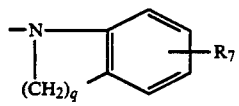

wherein q is an integer 2 to 5 and $R_7$ has the same meaning as $R_5$,

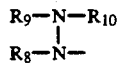

wherein $R_8$ and $R_9$ each are hydrogen, alkyl usually having 1 to 6 carbon atoms or

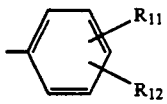

wherein $R_{11}$ and $R_{12}$ have the same meaning as $R_5$ and $R_6$ and $R_{10}$ is —COR$_{13}$, —CSR$_{13}$ or —SO$_2$R$_{13}$ wherein $R_{13}$ is hydrogen, alkyl usually having 1 to 6 carbon atoms, phenyl, —NH$_2$, —NHR$_{14}$, —N(R$_{14}$)$_2$ or —OR$_{14}$ wherein $R_{14}$ is hydrogen, alkyl usually containing 1 to 6 carbon atoms or phenyl. Representative alkyl groups include methyl, ethyl, propyl, butyl and hexyl. Representative β-substituted ethyl groups include β-methoxymethoxyethyl and β-2'-tetrahydropyranyloxyethyl. Representative aralkyl groups include phenyl and naphthyl-substituted alkyl, such as, benzyl, phenethyl and naphthylmethyl and representative alkaryl groups include alkyl-substituted phenyl and naphthyl, such as, o-merhylphenyl, o-methylnaphthyl and p-hexylphenyl. Representative carbocyclic aryl groups include phenyl and naphthyl and representative cycloalkyl groups include cyclopentyl, cyclohexyl and cycloheptyl. It will be appreciated that the auxochromic substituent(s) will be selected for a given diarylmethane, triarylmethane or bridged triarylmethane compound to provide the desired chromophore color upon opening of the S-containing ring and to achieve facile color formation.

In addition to the auxochromic substituents, the subject dye precursor compounds may possess one or more additional substituents on Z and/or Z' and/or ring B as may be desired that do not interfere with the intended utility for the dye. Typical substituents include carboxy; hydroxy; cyano; thiocyano; mercapto; sulfo; nitro; sulfonamido (—NHSO$_2$R$_0$); sulfamoyl (—SO$_2$NHR$_0$); sulfonyl (—SO$_2$R$_0$); acyl (—COR$_0$); carbamyl (—CONR$_0$); halomethyl such as trifluoromethyl; alkyl usually having 1 to 20 carbon atoms such as methyl, octyl, hexadecyl; alkoxy usually having 1 to 20 carbon atoms such as methoxy, ethoxy, propoxy and butoxy; alkoxycarbonyl having 1 to 20 carbon atoms such as ethoxy- and dodecyloxycarbonyl; aralkyl usually having 7 to 15 carbon atoms, for example, phenyl- or naphthyl-substituted aklyl such as benzyl, phenethyl and naphthylmethyl; alkaryl usually having 7 to 15 carbon atoms, for example, alkyl substituted phenyl or naphthyl such as o-methylphenyl, o-methylnaphthyl and p-hexylphenyl; aralkyloxy usually having 7 to 15 carbon atoms, for example, phenyl- or naphthyl-substituted alkoxy such as benzyloxy, phenethyloxy and naphthylmethyloxy; aryloxy usually containing 6 to 12 carbon atoms such as phenoxy and naphthoxy; thioalkyl groups, usually having 1 to 20 carbon atoms such as methylthio, ethylthio and hexylthio; thioaryl and thioaralkyl groups containing up to 15 carbon atoms such as phenylthio, naphthylthio, benzylthio and phenethylthio; halo such as chloro, bromo, fluoro and iodo; amino including mono- and disubstituted amino such as —NR$_{15}$R$_{16}$ wherein $R_{15}$ and $R_{16}$ each are hydrogen, alkyl usually having 1 to 20 carbon atoms, aralkyl usually having 7 to 15 carbon atoms and aryl having 6 to 12 carbon atoms; and a fused substituent such as a fused benzene ring.

The dye precursor compounds used in the present invention can be monomeric or polymeric compounds. Suitable polymeric compounds are those which, for example, comprise a polymeric backbone chain having dye precursor moieties attached directly thereto or through pendant linking groups. Polymeric compounds of the invention can be provided by attachment of the dye precursor moiety to the polymeric chain via the Z and/or Z' moieties or the ring B. For example, a monomeric dye precursor compound having a reactable substituent group, such as an hydroxyl or amino group, can be conveniently reacted with a mono-ethylenically unsaturated and polymerizable compound having a functional and derivatizable moiety, to provide a polymerizable monomer having a pendant dye precursor moiety. Suitable mono-ethylenically unsaturated compounds for this purpose include acrylyl chloride, methacrylyl chloride, methacrylic anhydride, 2-isocyanatoethyl methacrylate and 2-hydroxyethyl acrylate, which can be reacted with an appropriately substituted dye precursor compound for production of a polymerizable monomer which in turn can be polymerized in known manner to provide a polymer having the dye precursor compound pendant from the backbone chain thereof.

In this manner, a dye precursor compound having the structure illustrated in Example 15 hereof can be reacted with 2-isocyanatoethyl methacrylate for production of the corresponding urethane derivative via reaction of the respective hydroxyl and isocyanate groups. The desired polymer can then be obtained by free-radical initiated addition polymerization, using a free-radical catalyst such as α,α'-azodiisobutyronitrile (AIBN) according to known methodology. It will be appreciated, however, that other dye precursor compounds can be attached via other means to other polymerizable compounds for the production of other polymeric compounds having the desired property of forming color with Lewis acids, particularly heavy metal ions as discussed above.

Preferred compounds for use in the present invention are those represented by the formula

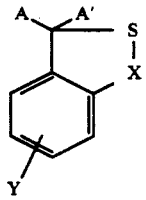
(II)

wherein X is

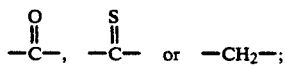

Y is hydrogen, alkyl having 1 to 6 carbon atoms, alkoxy having 1 to 6 carbon atoms, alkoxycarbonyl having 1 to 6 carbon atoms, carboxy, cyano, thiocyano, nitro, sulfo, sulfonamido, sulfamoyl, sulfonyl, acyl, carbamyl, halo, —OR wherein R is hydrogen, alkyl having 1 to 6 carbon atoms, benzyl or phenyl, —SR$_0$ wherein R$^0$ has the same meaning as R or —NR$^5$R$^6$ wherein R$^5$ and R$^6$ each are hydrogen, alkyl having 1 to 6 carbon atoms, β-substituted ethyl, benzyl or phenyl; A and A', the same or different, are selected from phenyl substituted in the 4-position with —OR$^1$ wherein R$^1$ has the same meaning as R, —SR$^2$ wherein R$^2$ has the same meaning as R or —NR$^5$R$^6$ wherein R$^5$ and R$^6$ have the same meaning given above and substituted in the 2-, 3-, 5- and 6-positions with hydrogen, alkyl having 1 to 6 carbon atoms, alkoxy having 1 to 6 carbon atoms or chloro or substituted in the 5- and 6-positions with a fused benzene ring; indol-3-yl substituted in the 1 and 2 positions with hydrogen, alkyl having 1 to 6 carbon atoms, benzyl or phenyl; pyrr-2-yl substituted in the 1-position with hydrogen, alkyl having 1 to 6 carbon atoms, benzyl or phenyl; and carbazol-3-yl substituted in the 9-position with hydrogen, alkyl having 1 to 6 carbon atoms, benzyl or phenyl and A and A' taken together represent phenyl groups bridged by a heteroatom selected from oxygen, sulfur and nitrogen substituted with hydrogen or alkyl having 1 to 6 carbon atoms to form xanthene, thioxanthene or acridine (a) substituted in the 3- and 6-positions with a group, the same or different, selected from —OR$^3$ wherein R$^3$ has the same meaning as R, —SR$^4$ wherein R$^4$ has the same meaning as R and —NR$^7$R$^8$ wherein R$^7$ is hydrogen or alkyl having 1 to 6 carbon atoms and R$^8$ is alkyl having 1 to 6 carbon atoms, benzyl or

wherein R$^9$ and R$^{10}$ each are hydrogen, alkyl usually having 1 to 6 carbon atoms, alkoxy having 1 to 6 carbon atoms, chloro, nitro, cyano, alkoxycarbonyl wherein said alkoxy has 1 to 6 carbon atoms, sulfonamido, sulfamoyl, sulfonyl, acyl, or carbamyl and R$^9$ and R$^{10}$ taken together represent indolino, indolino substituted with acyl or

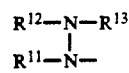

wherein R$^{11}$ and R$^{12}$ each are hydrogen, alkyl having 1 to 6 carbon atoms or

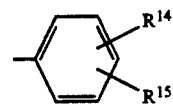

wherein R$^{14}$ and R$^{15}$ have the same meaning as R$^9$ and R$^{10}$ and R$^{13}$ is —COR$^{16}$ wherein R$^{16}$ is hydrogen, alkyl having 1 to 6 carbon atoms or phenyl and substituted in the 1-, 2-, 4-, 5-, 7- and 8-positions with hydrogen, alkyl having 1 to 6 carbon atoms, alkoxy having 1 to 6 carbon atoms or chloro or (b) substituted in the 3-position with —NR$^{17}$R$^{18}$ wherein R$^{17}$ is hydrogen, alkyl having 1 to 6 carbon atoms, cycloalkyl having 5 to 7 carbon atoms, benzyl or phenyl and R$_{18}$ is alkyl having 1 to 6 carbon atoms, cycloalkyl having 5 to 7 carbon atoms, benzyl or phenyl and R$_{17}$ and R$_{18}$ taken together represent piperidino, pyrrolidino, N-methylpiperidino or indolino and (1) substituted in the 7- and 8-positions with a fused benzene ring or (2) substituted in the 7-position with hydrogen, —NR$^{17}$R$^{18}$ wherein R$^{17}$ and R$^{18}$ have the same meaning given above, alkyl having 1 to 6 carbon atoms, alkoxy having 1 to 6 carbon atoms or chloro and substituted in the 1-, 2-, 4-, 5-, 6- and 8-positions with hydrogen, alkyl having 1 to 6 carbon atoms, alkoxy having 1 to 6 carbon atoms or chloro. Preferably, X is

The di- and triarylmethane thiolactone dye precursors of the foregoing formulae can be synthesized from the corresponding lactones by heating substantially equimolar amounts of the lactone and phosphorus pentasulfide to reflux in pyridine or other suitable solvent or by heating with phosphorus heptasulfide in tetrahydrofuran or other solvent. Under these conditions, the thiolactone together with the dithiolactone are obtained as the two major products of the reaction which are then recovered from the reaction mixture, for example, by precipitation and then isolated using conventional techniques such as column chromatography. If desired, the dithiolactone may be converted to the thiolactone by oxidation using, for example, hydrogen peroxide. Conversely, the thiolactone may be converted to the dithiolactone by further reaction with phosphorus pentasulfide.

It is quite surprising that the subject thiolactones, particularly, the thiophthalide dye precursors can be synthesized directly from the corresponding phthalides using phosphorus pentasulfide or its equivalent, since the products obtained by reacting fluorane, fluorescein-chloride and diphenylphthalide with phosphorus pentasulfide gave only the corresponding dithiophthalides as reported by R. Meyer, ibid. and I. P. Soloveichik, et al., ibid. It is believed that the unexpected formation of thiophthalide in admixture with dithiophthalide is due to the electronic effects of an auxochromophoric system in the starting phthalide which is absent in the starting materials used previously. Presumably, the auxochromic function through resonance and inductance stabilizes the incipient carbonium ion forming the charge center of the open dye form to impart special reactivity to the starting phthalide. In this regard, it is well known that the leuco-phthalide dye-formers used as starting materials can be readily converted to their conjugate dye-acid form as illustrated below in scheme (i). Fluorane, fluoresceinchloride and diphenylphthalide are not comparably sensitive.

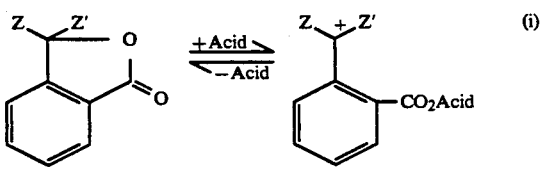

wherein Z and Z' have the same meaning given above.

Presumably, this property of the leuco-phthalide starting materials also provides the basis for the preferred synthesis of the dye precursors of the thiolactone type. According to this method, di- and triarylmethane thiophthalide dye precursors, for example, can be obtained substantially free of dithiophthalide via "an activating intermediate complex" which is "trapped" with sulfide by reaction with, for example, NaHS XH$_2$O, Na$_2$S or H$_2$S to yield the corresponding thiophthalide as illustrated below.

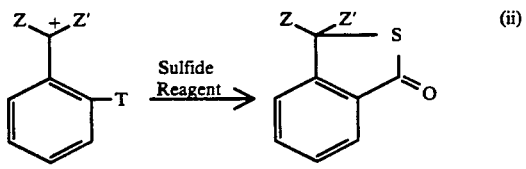

wherein T is preferably —COCl or —COE wherein E is alkyl having 1 to 4 carbon atoms or benzyl and Z and Z' have the same meaning given above.

The leuco-phthalide starting material can be converted to the corresponding dye-acid chloride or dye-ester intermediate in a known manner. For example, Stadler, Paul Albert, Helvitica Chimica Acta, Vol. 61, Fasc. 5 (1978), No. 162, p. 1675, reports the reaction of oxalylchloride with dimethylformamide in a suitable solvent to give dimethylformamide imide chloride followed by the addition of an acid to this suspension to furnish an activated carboxy-group derivative. The activated carboxy-group derivative is then transformed to an ester by addition of pyridine and an alcohol or phenol. Chandrasekaran, S. and John V. Turner, Synthetic Communications, 12(9), pp. 727-731 (1982) describe carboxy group activation at −30° to −20° C. using methane sulfonyl chloride and triethylamine and then treating the intermediate mixed anhydride in situ with an alcohol to give the ester. It is noted that dimethyl aminopyridine catalysis may be used to enhance esterification rates. Also, the authors note that the procedure can be used to prepare thiol esters or amides.

In the subject method, the leuco-phthalide starting material is reacted with a slight excess, usually a 0.2 to 0.3 molar excess of an acid chloride such as thionyl or oxalyl chloride in a suitable organic solvent. The solvent employed can be readily selected for the given reactants. Typical solvents include methylene chloride, acetonitrile and pyridine. When thionylchloride is employed, dimethylaminopyridine may be used to catalyze the reaction. The reaction temperature usually varies between about −20° and 20° C.

The —COCl intermediate thus formed is then reacted with a sulfide reagent, such as, hydrogen sulfide, sodium sulfide or sodium hydrogen sulfide or its hydrate. The sulfide reagent may be added to the reaction solution containing the intermediate or the solution containing the intermediate may be added to a solution of the sulfide reagent dissolved in a suitable solvent. Preferably, the reaction solution of activated intermediate is quenched into a methanol solution of sodium hydrogen sulfide hydrate. The temperature for the reaction between the intermediate and sulfide reagent usually varies between about −20° and 20° C. If desired, the —COCl intermediate can be isolated before the reaction with the sulfide reagent, and if desired, the —COCl intermediate can be converted to the corresponding ester by reaction with an alkanol or benzyl alcohol prior to reaction with the sulfide reagent. Also, the starting lactone can be converted directly to the ester by acid esterification using an acidified alcohol, for example, by refluxing the lactone in benzyl alcohol or a 1-4 carbon alkanol acidified with a mineral acid and the —COE intermediate reacted with the sulfide reagent as above.

The above reactions to form a thiophthalide or other thiolactone dye precursor are not usual or general to all lactones, such as, simple lactones and non-dye forming phthalides. For example, it has been found that 2,2-disubstituted phthalide non-dye formers such as diphenylphthalide and fluoresceinchloride cannot be converted to their thiophthalides through an activating intermediate. Their lack of reactivity with oxalylchloride under the above described conditions presumably is due to the absence of an auxochromic function. As mentioned previously, it is believed that the property of the leuco-phthalide dye formers to be easily converted to their conjugate dye-acid forms the basis for this new synthesis. As to simple lactones, the synthetic route reported by Kaloustian, M. K. and F. Khouri, Tetrahedron Letters, Vol. 22, p. 413-416 (1981) shows that simple lactones undergo O-alkylation with Meerwein's salts to form an intermediate lactonium salt which when reacted with anhydrous sodium hydrosulfide in acetonitrile at 0° C. affords the corresponding thionolactone rather than thiolactones.

The thioether compounds may be synthesized, for example, by reducing both the lactone and the dye to the leuco form followed by halogenating the alcohol and reacting the latter compound with thiolpropionic acid, then oxidizing the leuco dye and treating with base to give the desired thioether product.

Starting materials useful in synthesizing the above-denoted dye precursors are the corresponding lactones of the compounds defined in formulae I and II above. Lactone compounds are well known in the art and may be synthesized using various conventional methods. Indeed, numerous di- and triarylmethane dyes including bridged triarylmethanes possessing a lactone ring-closing moiety or capable of being derivatized with a lactone ring-closing moiety have been described in Venkataraman, K., The Chemistry of Synthetic Dyes, Academic Press, Inc., New York, 1952, pp 705-760 and 1111 and in U.S. Pat. Nos. 3,491,111; 3,491,112; 3,491,116; 3,509,173; 3,509,174; 3,514,310; 3,514,311; 3,775,424; 3,853,869; 3,931,227; 3,959,571; 4,267,251, 4,535,172 4,341,403 and 4,535,348. If the lactone starting materials possess hydroxy, carboxy, mercapto or other substituents that may require blocking during synthesis, conventional protecting groups may be employed as described by McOmie, J. F. W., Protective Groups in Organic Chemistry, Plenum Press, New York, 1973 and by Greene, Theodora W., Protective Groups in Organic Synthesis, John Wiley & Sons, New York, 1981.

The following examples are given to further illustrate the present invention and are not intended to limit the scope thereof. It will be understood that the ring-closed thiolactone, dithiolactone and thioether compounds are substantially colorless and in their ring-opened form give the chromophore color indicated in the examples.

Also, it will be understood that in the following examples, Me Cell denotes 2-methoxyethanol, TMS denotes tetramethylsilane, $CDCl_3$ denotes deuterochloroform, MeOH denotes methanol, and that E represents the extinction coefficient at the wavelength indicated.

EXAMPLE 1

Preparation of the compounds having the formulae

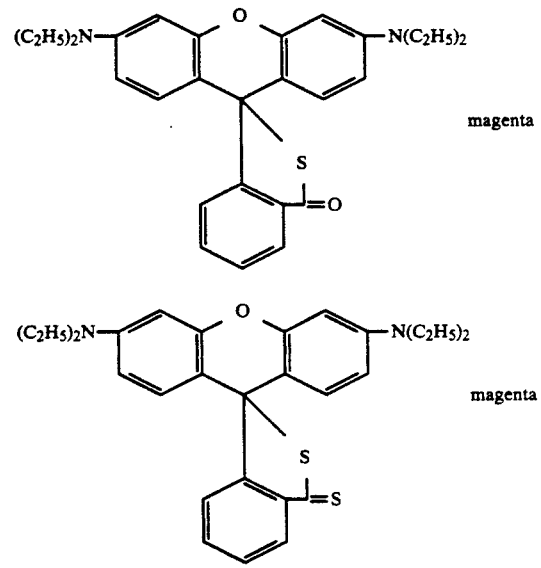

Rhodamine B (10 g; 0.02 mol) and phosphorus pentasulfide (4.6 g; 0.02 mol) were heated to reflux in pyridine (250 ml) for four hours. The cooled solution was quenched in 500 g ice - 250 ml concentrated hydrochloric acid. The pH was adjusted to pH 5 with aqueous sodium hydroxide. The solid was collected and air dried. The crude was purified by chromatography (silica gel, methylene chloride) to yield two major products, 5 g of the thiolactone compound of formula 1a as a tan solid and 1.5 g of the dithiolactone compound of formula 1b as a red crystalline solid.

Compound 1a

UV (Me Cell) $\lambda_{max}$ 237 nm (E=66,000) 282 nm (E=33,600) 319 nm E=17,200). IR (KBr, cm$^{-1}$) 1675, 1608. NMR: ($CDCl_3$, TMS)δ6.2-7.8m (10H, m), 3.25 (8H, q), 1.1 (12H, t)

Anal. Calc. for $C_{28}H_{30}N_2SO_2$: C, 73.4; H, 6.5; N, 6.1; S, 7.0; O, 7.0. Found: C, 73.51; H, 6.76; N, 6.0; S, 6.87.

Compound 1b

UV (Me Cell) $\lambda_{max}$ 240 nm (E=58, 400), 285 nm (E=35,200), 324 nm (E=30,000), 415 nm (E=1,600). IR (KBr, cm$^{-1}$) 1618.

Anal. Calc. for $C_{28}H_{30}N_2S_2O$: C, 70.1; H, 6.3; N, 5.9; S, 13.5; O, 3.4. Found: C, 70.6; H, 6.5; N, 5.8; S, 13.2.

EXAMPLE 2

Preparation of the compounds having the formulae

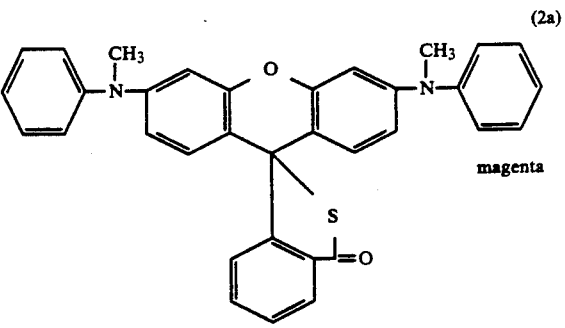

and

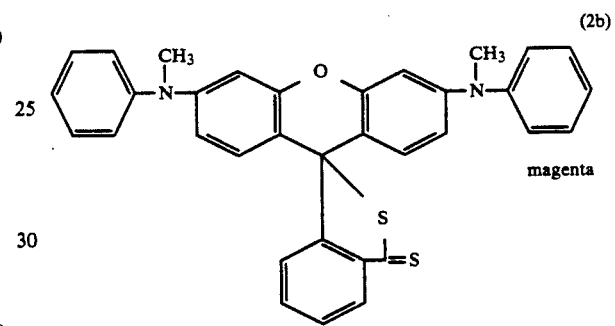

The title compounds were prepared from the corresponding phthalide following the procedure given in Example 1.

Compound 2a

UV (Me Cell) $\lambda_{max}$ 238 nm (E=52,200), 303 nm (E=26,800). IR (KBr, cm$^{-1}$) 1682, 1598. NMR ($CDCl_3$, TMS) δ 6.2-7.7 (30H, m), 3.2 (6H, s).

Anal. Calc. for $C_{34}H_{26}N_2O_2S$: C, 77.6; H, 4.9; N, 5.3; S, 6.08. Found: C, 77.89; H, 5.13; N, 5.19; S. 5.89.

Compound 2b

UV (Me Cell) $\lambda_{max}$ 238 nm (E=50,000), 306 nm (E=31,600), 415 nm (E=1000). IR (KBr, cm$^{-1}$) 1590. M/e 452

EXAMPLES 3-11

The following thiophthalides were prepared from the corresponding phthalide following the procedure given in Example 1.

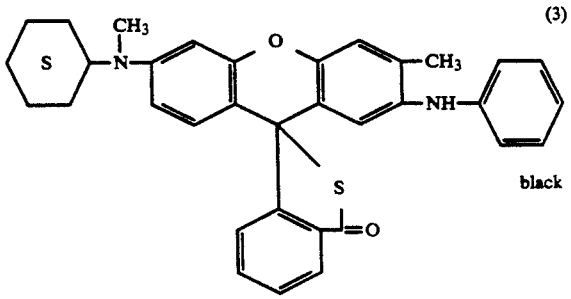

UV (Me Cell) λ$_{max}$ 236 nm (E=37,600), 281 nm (E=35,200), 315 nm (E=15,200).

IR (KBr, cm$^{-1}$) 1680, 1603

NMR (CDCl$_3$, TMS)δ6.2-7.9 (14H, m), 5.15 (1H, s), 3.5 (1H, s), 2.7 (3H, s), 2.15 (3H, s), 0.9-1.9 (11H, m). M/e 532.7

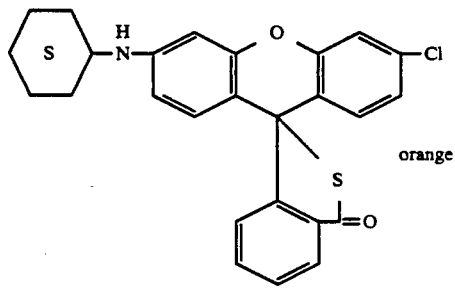

(4)

orange

IR (KBr, cm$^{-1}$) 1690, 1630, 1600.

UV (Me Cell) λ$_{max}$ 233 nm (E=43,200), 282 nm (E=17,600), 315 nm (E=6,600).

VIS (MeOH, 10 mgAgNO$_3$) λ$_{max}$ 450 nm (E=24,000), 474 nm (E=33,200), 500 nm (E=27,200).

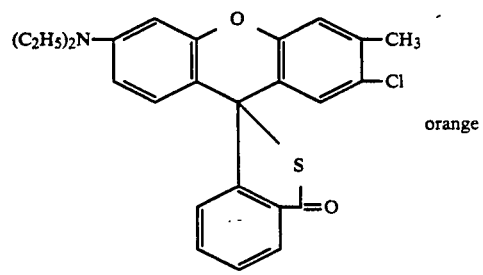

(5)

orange

NMR (CDCl$_3$, TMS)δ6.2-8.0 (m, 9H, 3.3 q, J=3 Hz. 4H) 2.3 (2,3H), 1.2 (t, J≈3 Hz, 6H).

IR (KBr, cm$^{-1}$) 1692, 1637, 1618.

UV (Me Cell) λ$_{max}$ 236nm E=40,000), 285 nm (E=16,800), 325 nm (E=7,300).

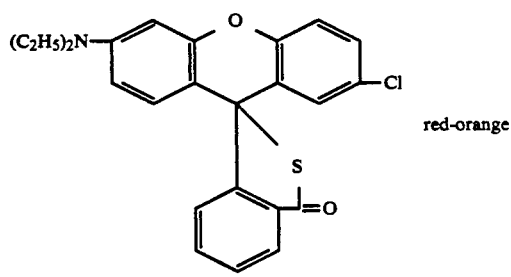

(6)

red-orange

NMR(CDCl$_3$, TMS) δ6,8-8.0 (m, 10H), 3.3 (q, J=3 Hz, 9H), 1.15 (t, J≈3 Hz, 6H).

IR (KBr, cm$^{-1}$) 1680, 1630.

UV (Me Cell) λ$_{max}$ 237 nm (E=37,400), 281 nm (E=18,800), 325 nm (E=6,900).

Vis (MeOH, 10 mg AgNO$_3$) λ$_{max}$ 480 nm (E=23,600), 497 nm (E=29,600), 530 nm (E=23,200).

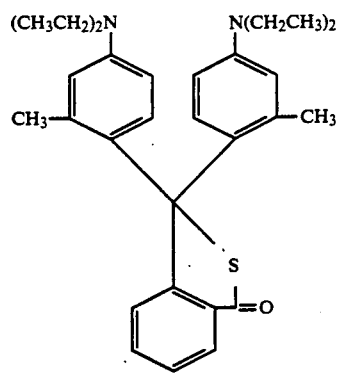

(7)

green

NMR (CDCl$_3$, TMS)δ6.3-8.0 (m, 10H), 3.3 (q, J≈3H, 8H), 2.2 (s, 3H), 1.95 (s, 3H), 1.15 (t, J=3 Hz, 12H). IR (CH$_2$Cl$_2$, cm$^{-1}$) 1674, 1605.

Anal. Calc. for C$_{28}$H$_{36}$N$_2$OS: C, 74.96; H, 8.09; N, 6.20; S, 7.15.

Found: C. 74.83, H, 7.56; N, 5.78; S, 6.91.

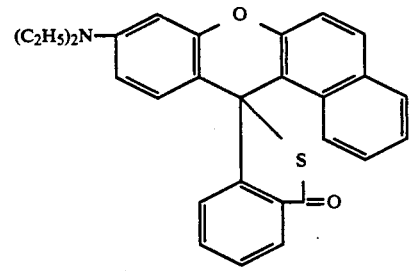

(8)

red

NMR (CDCl$_3$ TMS)δ6.3-8.2 (m, 13H), 3.4 (q, J≈3 Hz, 4H), 1.20 (t, J≈3 Hz, 6H).

IR (KBr, cm$^{-1}$) 1678, 1627.

UV (Me Cell) λ$_{max}$ 252 nm (E=58,800), 283 nm (E=25,800), 325 nm (E=6,600).

VIS (MeOH, 10 mg AgNO$_3$) λ$_{max}$ 490 nm (E=26,400), 520 nm (E=40,000), 554 nm (E=36,400).

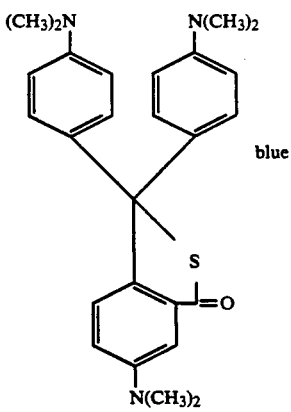

(9)

blue

VIS (MeOH, 10 mg AgNO$_3$) λ$_{max}$ 604 nm (E=57,600).

UV (Me Cell) λ$_{max}$ 275 nm (E=50,000), 380 nm (E=2,200).

IR (KBr, cm$^{-1}$) 1678, 1618. M/e 431.6

Anal. Calc. for C$_{26}$H$_{29}$N$_3$OS: C, 72.36; H, 6.77; N, 9.71; S, 7.43.

Found: C, 72.246; H, 6.33; N, 9.48; S, 7.69.

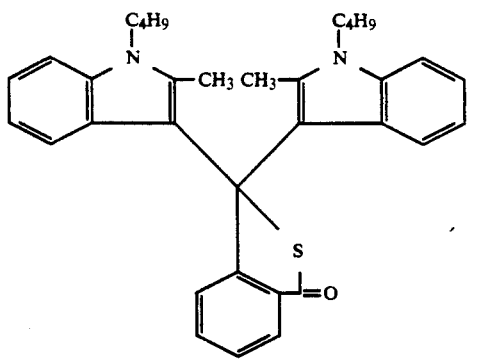

magenta (10)

VIS (MeOH, 10 mg AgNO$_3$) $\lambda_{max}$ 535 nm (E=34,400).
UV (Me Cell) $\lambda_{max}$ 284 nm (E=18,800).
IR (KBr, cm$^{-1}$) 1678.

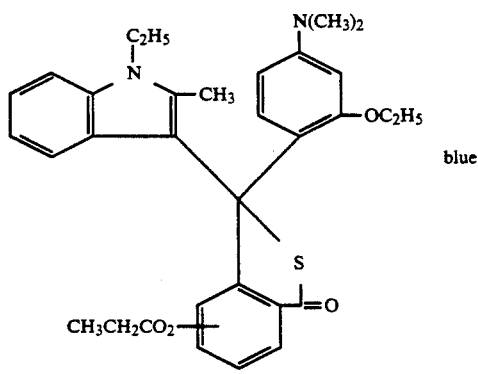

blue (11)

IR (KBr, cm$^{-1}$) 1720, 1670, 1605.
UV (MeOH) $\lambda_{max}$ 255 nm (E=22,400), 275 nm (E=28,000).
VIS (MeOH, 10 mg AgNO$_3$) $\lambda_{max}$ 583 nm (E=50,000).

As in Examples 1 and 2 above, the dithiophthalides corresponding to the thiophthalides of Examples 3 to 11 also were obtained. Typically, the thiophthalides are recovered as colorless or lightly colored solids and the dithiophthalides as reddish solids.

EXAMPLE 12

Preparation of the compound having the formula

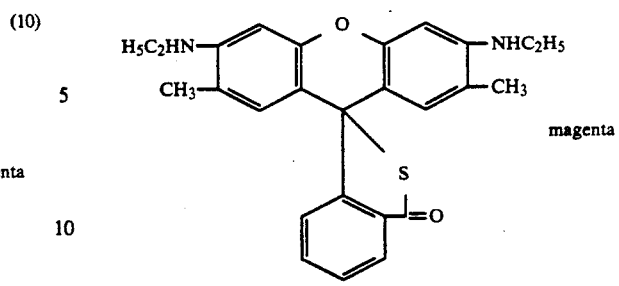

magenta

To Rhodamine 6G (0.5 g, 0.001 mol) in a solution of acetone (20 ml) and water (5 ml) at a temperature between room temperature and −10° C. was added sodium hydrosulfide hydrate dropwise initially, then 1 ml at a time. The mixture was kept at −10° C. for 1.5 hours during which time a pink precipitate formed. The mixture was allowed to warm to room temperature to determine if it would effect precipitate formation. The mixture was refrigerated overnight. Impurities that coprecipitated with the product were removed by washing with hot methanol. The solution was filtered (hot) under suction and the title compound recovered as a pink solid was dried under vacuum (50° C.). The compound was identified by NMR (CDCl$_3$—D$_2$O) and by UV (MeOH, AgNO$_3$—10%).

The Rhodamine 6G used as the starting material in the foregoing example has the formula

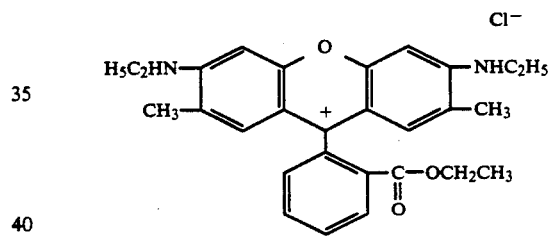

EXAMPLE 13

Preparation of the compound having the formula

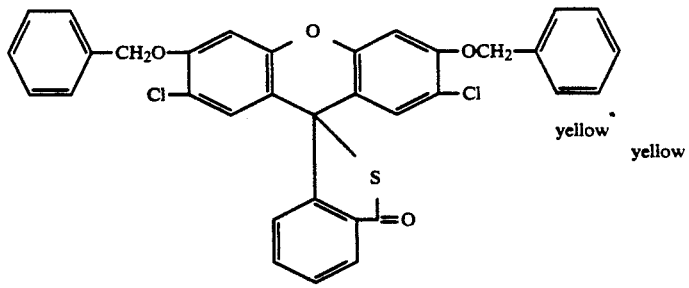

yellow

To 2,7-dichlorofluorescein (2.0 g., 0.005 mol) in acetone (30 ml) was added potassium carbonate (4.1 g, 0.0296 mol). While stirring, α-bromotoluene (1.9 ml, 0.0111 mol) was added dropwise and the solution was allowed to reflux for 2.5 hours, during which time an unidentified pinkish solid was generated. One equivalent of α-bromotoluene was added after 3.5 hours. The solution was stirred continuously for 18 hours and then filtered to give the alkylated ester intermediate of the formula

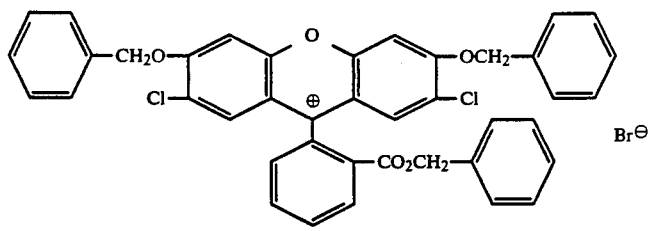

A concentrated solution of sodium hydrogen sulfide hydrate (3 g. in 7 ml water) was added dropwise to a solution of the alkylated ester intermediate in 50 ml acetone at room temperature. After 1.5 hours additional sodium hydrogen sulfide hydrate was added (6 g. in 10 ml water). Several grams of dry NaSH was then added and the mixture was stirred for another hour. A moderate volume of ethyl acetate and saturated aqueous sodium chloride solution was added. The ethyl acetate layer was extracted with distilled water and dried over sodium sulfate. The organic layer was then evaporated to give the crude title compound as a yellow-orange solid which was dried under vacuum.

EXAMPLE 14

Preparation of the compound having the formula

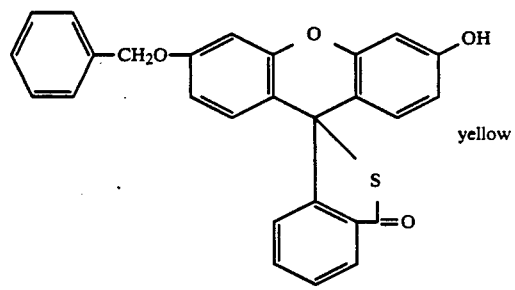

The title compound was prepared in the same manner described in Example 13 by alkylating fluorescein with α-bromotoluene to give the ester intermediate of the formula

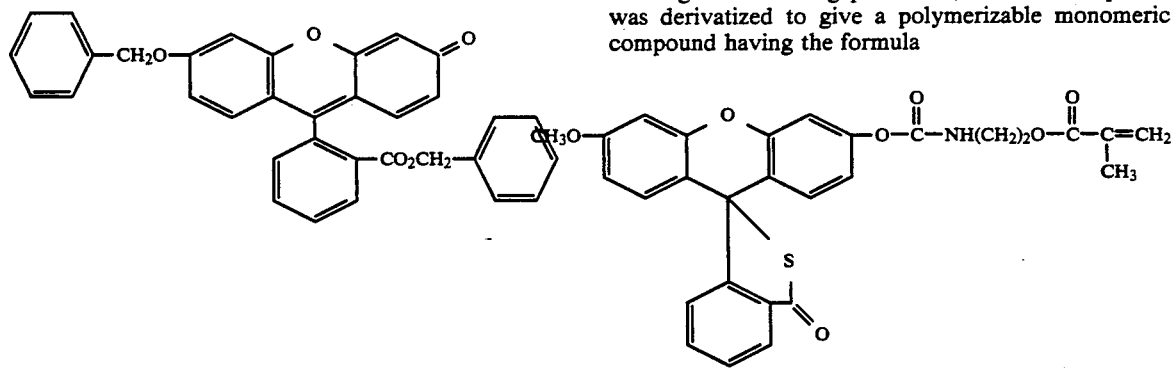

followed by reacting the intermediate with NaHS in methanol solution.

EXAMPLE 15

Preparation of the compound having the formula

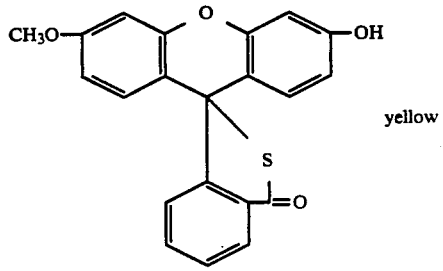

The title compound was prepared in the same manner described in Example 13 by alkylating fluorescein with methyltosylate to give the ester intermediate of the formula

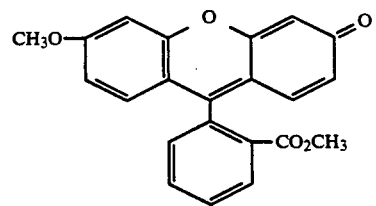

followed by reacting the intermediate with NaHS in methanol solution.

Using the following procedure, the title compound was derivatized to give a polymerizable monomeric compound having the formula

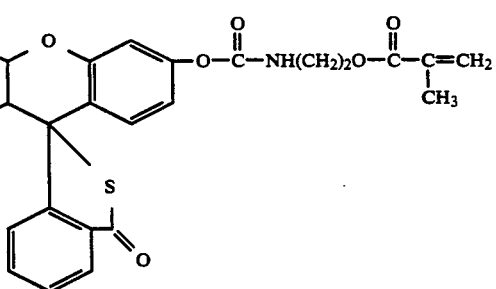

The compound of Example 15 (1.74 g, 4.81 mmol) was placed in a 100 ml round bottom flask and dissolved upon reflux in methylene chloride (60 ml). Isocyanatoethyl methacrylate (7.2 mmol, 1.02 ml) and a catalytic amount of dibutyltin diacetate was added to the refluxing solution. A quantitative yield of the crude product was obtained. Purification was accomplished by reducing the volume of the reaction mixture in vacuo. The reaction concentrate was applied onto a packed column of silica gel and eluted with methylene chloride. The complete removal of solvent from the recovered elutent in vacuo yielded the monomeric compound as a light yellow solid. Yield 2.03 g (82% by weight).

EXAMPLE 16

Preparation of the compound having the formula

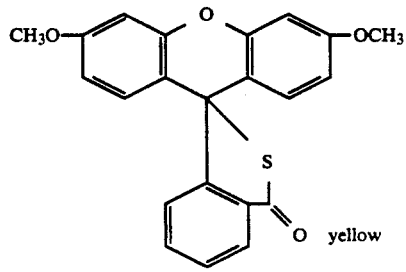

The title compound was prepared by reacting one equivalent of the compound prepared in Example 15 with about four equivalents of dimethylsulfate at reflux in acetone solution containing five equivalents of potassium carbonate.

EXAMPLE 17

Preparation of the compound having the formula

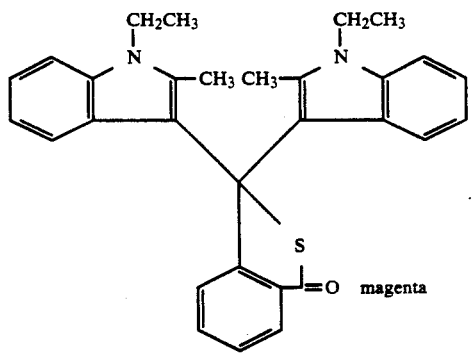

To a solution of 1 gram of 3,3-bis (1-ethyl-2-methylindol-3-yl) phthalide in 50 ml of methylene chloride was added 1 gram of oxalylchloride dropwise. Gas evolved immediately and a magenta solution was formed. After 2 hours, the solution was quenched in a solution of sodium hydrogen sulfide hydrate (2 grams) in methanol (30 ml). The magenta color was dispersed on mixing and a yellow solution resulted. The methylene chloride solution was washed with water, brine and dried over calcium sulfate. Solvent removal gave 1.2 grams of a crude yellow solid which was purified by silica chromatography to yield pure title compound.

EXAMPLE 18

The thiophthalide compound of Example 9 also was prepared as follows:

(a) A three-liter three-neck round bottom flash equipped with an overhead stirrer, nitrogen inlet and thermometer was charged with dimethylaminopyridine (70 g., 0.57 mol) and reagent grade acetonitrile (2 liters).

The solution was cooled to an internal temperature of −20° C. at which point some minor crystallization of the pyridine occurred. Thionylchloride was added dropwise (69 g., 0.58 mol) over 20 minutes via addition funnel at a reaction temperature of −20° C. A white dispersion formed. The reaction was stirred at −20° C. for 15 minutes. Solid Crystal Violet Lactone (200 g., 0.48 mol) was added to the reaction at which point the dispersion turned blue. The reaction mixture was allowed to warm to 0° C. over 20 minutes and maintained at 0° C. for 2 hours.

(b) The blue solution was then added to a 0° C. solution of sodium hydrogen sulfide (200 g) in methanol (2 liters). The tan dispersion was diluted with water (4 liters) and then filtered. The solid was washed with water (2×4 liters) and dried. The crude was purified by high pressure liquid chromatography to yield 150 g of pure title compound as a light yellow solid.

In a further preparation, step (a) was repeated and then gaseous hydrogen sulfide was passed through the blue solution of acid chloride intermediate for one hour. The solution was further treated with gaseous hydrogen sulfide for 12 hours. The solid that formed was collected by filtration, and the crude material was purified by high pressure liquid chromatography to give 50% overall yield of pure title compound on a 10 gram scale.

Rather than adding the Crystal Violet Lactone to the thionyl chloride, step (a) was carried out by dissolving 0.25 mol of Crystal Violet Lactone in 250 ml of methylene chloride at room temperature, cooling the solution to 0° C. under nitrogen and then adding 0.26 mol of thionyl chloride at a rate to maintain the reaction temperature between 0 and 5° C. The reaction mixture became dark blue and after stirring under nitrogen at 0°-5° C. for two hours, the solution was added to a solution of sodium hydrogen sulfide in 250 ml methanol at a rate to maintain the temperature of the sodium hydrogen sulfide solution below 5° C.

EXAMPLE 19

The thiophthalide compound of Example 7 was prepared from the corresponding phthalide according to the procedure of steps (a) and (b) given in Example 18 above and yielded 35g of pure compound on a 50g scale.

EXAMPLE 20

The thiophthalide compound of Example 10 was prepared from the corresponding phthalide according to the procedure of steps (a) and (b) given in Example 18 above except methylene chloride was used as the solvent instead of acetonitrile in step (a) and the phthalide starting material was added as a methylene chloride solution. Pure title compound was obtained in 92% yield by extraction rather than chromatography.

EXAMPLE 21

Preparation of the compound having the formula

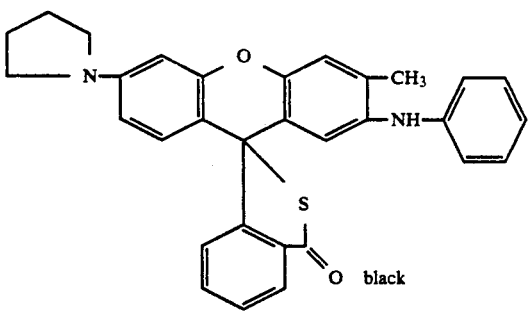

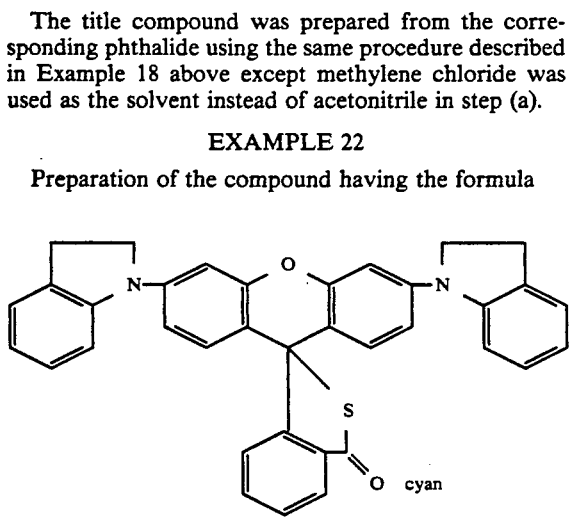

The title compound was prepared from the corresponding phthalide using the same procedure described in Example 18 above except methylene chloride was used as the solvent instead of acetonitrile in step (a).

EXAMPLE 22

Preparation of the compound having the formula

The title compound was prepared from the corresponding phthalide according to the procedure given in Example 17 above.

EXAMPLE 23

Preparation of the compound having the formula

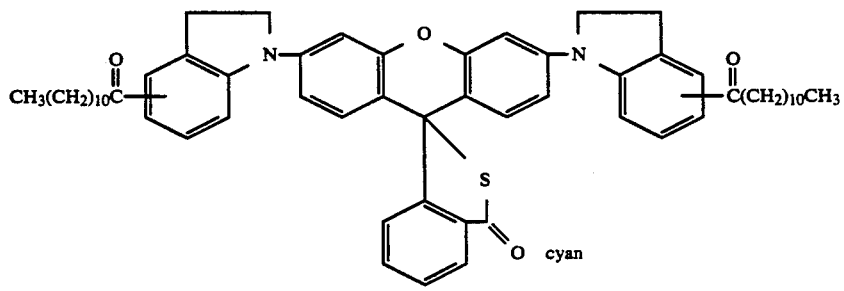

The title compound was prepared by reacting one equivalent of the compound prepared in Example 22 with 2.1 equivalents of lauryl chloride in methylene chloride solution containing 2.0 equivalents of stannic chloride.

EXAMPLE 24

The thiophthalide of Example 3 also was prepared by refluxing the starting phthalide in methanol (or n-butanol) acidified with sulfuric acid to give the corresponding ester having the formula

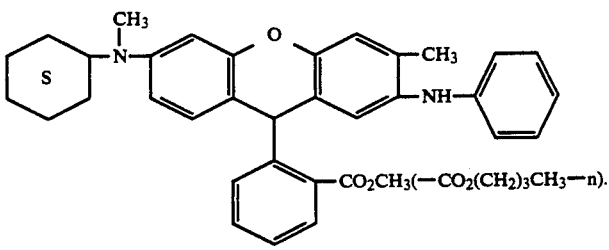

The reaction solution containing the ester intermediate was then added to a solution of sodium hydrogen sulfide in methanol at room temperature to give the corresponding thiophthalide.

EXAMPLE 25

Preparation of the compound having the formula

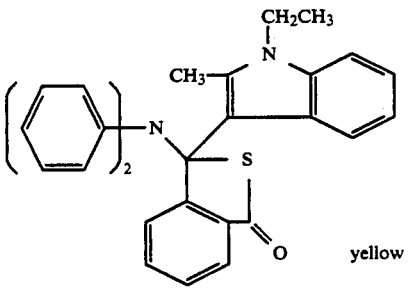

Oxalyl chloride (1.5., 0.012 mol) was added dropwise to a solution of the following phthalide (5 g., 0.011 mol) dissolved in methylene chloride at 0° C.

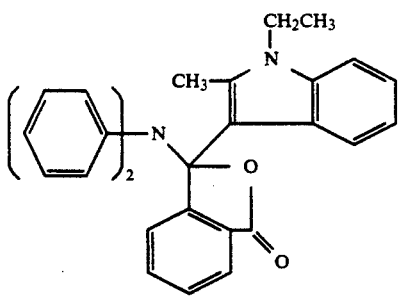

Foaming occurred. After 15 minutes, the reaction solution was added to a stirred solution of sodium hydrogen sulfide hydrate (5 g) in methanol (50 ml) and stirred for 20 minutes. The mixture was diluted with ether (300 ml) and washed with water, brine and dried over calcium sulfate. Solvent removal yielded 5 g of a crude orange solid. Purification on 30/60 micron silica, activity I yielded 3.2 g of a cream colored solid. M/e 474.6; Anal: Calc for $N_2OSC_{31}H_{26}$: C, 78.45; H, 5.52; N, 5.90; S, 6.76. Found: C, 78.05; H, 6.01; N, 5.36; S, 6.42.

EXAMPLE 26

Preparation of the compound having the formula

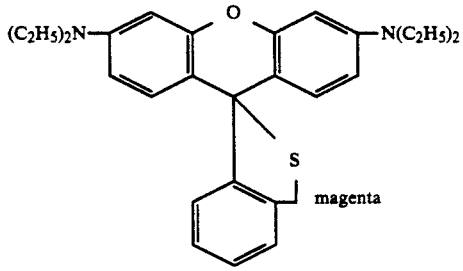

The acetoxymethyl derivative of Rhodamine B (0.5 g) having the formula

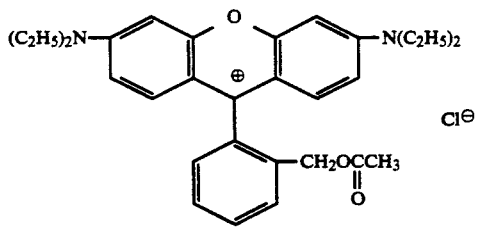

was heated to reflux with phosphorus pentasulfide (0.3 g) and pyridine (20 ml) for 2 hours. Ethyl ether (100 ml) was added to the warm solution and the residue triturated with ether (4×30 ml). The combined other extracts were chromatographed on a silica column using hexane eluent to give 200 mg of the title compound as a tan solid. NMR (CDCl$_3$, TMS) 7.7–6.1 (10H, m), 4.5 (s, 2H), 3.2 (q, 8H) and 1.2 (t, 12H). M/e (FAB) MH+ =445.6

EXAMPLE 27

Preparation of the compound having the formula

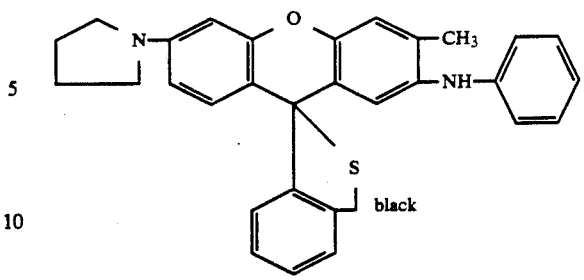

(a) A solution of 25 g (52.7 mmole) of the following lactone

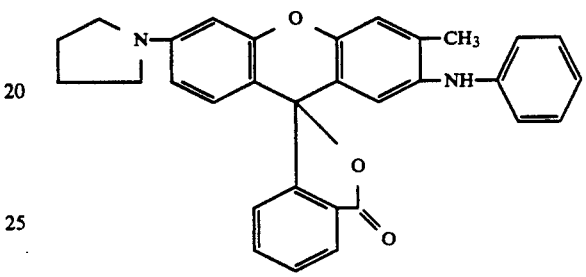

in 175 ml of dry tetrahydrofuran was added to a slurry of 7.97 g (0.21 mole) of lithium aluminum hydride in 250 ml of dry tetrahydrofuran under an atmosphere of nitrogen at room temperature. After addition, the mixture was allowed to stir at room temperature for 15 minutes then heated at reflux for 2 hours. The mixture was cooled to room temperature and then treated successively with 8 ml water, 8 ml 15% aqueous sodium hydroxide solution and 24 ml water. The precipitated salts were filtered and washed with a small amount of tetrahydrofuran. The filtrate was evaporated under reduced pressure and the residue dissolved in 200 ml ethylene chloride, washed with ½-saturated sodium chloride solution (2×200 ml) and dried over sodium sulfate. The solvent was evaporated under reduced pressure to afford a light-brown oil. This oil was triturated in 100 ml of absolute ethanol, heated at reflux at which point crystallization occurred. The mixture was cooled in an ice bath, the product filtered, washed with a small amount of ethanol and dried in vacuo to give 20.5 g. (84% by weight) of the intermediate having the formula

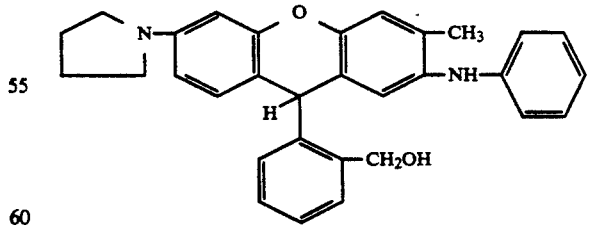

Hydrogen bromide was bubbled into 50 ml anhydrous methanesulfonic acid for 20 minutes at room temperature. Then 9.25 g (0.02 mole) of the intermediate of step (a) was added portionwise over a period of 2 to 3 minutes. The mixture was allowed to stir overnight at room temperature, then diluted with 100 ml chloroform, cautiously poured into 500 ml aqueous 5% sodium bicarbonate solution and transferred to a separatory funnel. The lower chloroform layer was separated, washed with 5% sodium bicarbonate solution (1×100 ml), ½-saturated sodium chloride solution (2×200 ml) and dried over magnesium sulfate. The magnesium sulfate was removed by filtration and the filtrate treated with 10 g silica gel to remove unreacted material. The silica gel was removed by filtration and the solvent evaporated from the filtrate under reduced pressure to afford an oil which was triturated in 100 ml of hot ethanol to induce crystallization. The mixture was cooled in an ice bath. The crystalline material was filtered, washed with a small amount of ethanol and dried in vacuo to give 9.84 g (94% by weight yield) of the following intermediate as an off-while solid.

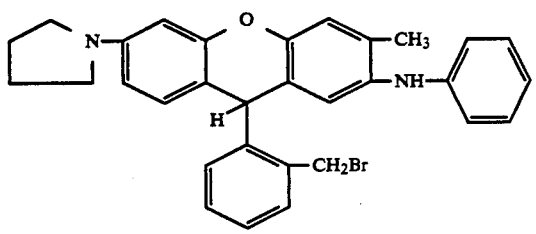

(c) To a mixture of 525.5 mg (1.0 mmole of the intermediate prepared in step (b) in 10 ml ethyl acetate was added 0.1 ml (100 mg, 1.1 mmole) of thiolpropionic acid and 0.155 ml (112 mg, 1.1 mmole) of triethylamine. The mixture was gently heated under an atmosphere of nitrogen. TLC on silica using 1:1 ethylene chloride/hexane after 4 hours indicated 75% conversion. Another 0.05 ml (approximately 50 mg., 0.55 mmole) of thiolpropionic acid and 0.078 ml (56 mg, 0.55 mmole) of triethylamine was added and the mixture allowed to stir under gentle reflux overnight under an atmosphere of nitrogen. TLC after overnight reflux showed very little starting material. The mixture was filtered to remove the triethylamine hydrobromide and washed with a small amount of ethyl acetate. The ethyl acetate solution was washed with water (2×25 ml), 5% sodium bicarbonate solution (3×25 ml), saturated sodium chloride solution and then dried over sodium sulfate. The mixture was filtered, the solvent evaporated from the filtrate under reduced pressure and the residue dried under high vacuum to give 572.6 mg of the following intermediate

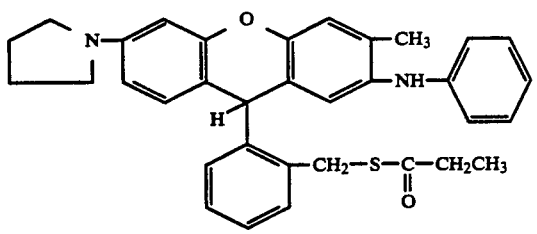

(d) A solution of 102.6 mg (0.19 mmole) of the intermediate prepared in step (c) in 10 ml methanol was treated with 50 mg (0.2 mmole) of o-chloranil. The mixture was heated to reflux for 2 hours. TLC indicated that conversion was substantially complete. Then 0.6 ml of aqueous 1.0N sodium hydroxide solution was added and refluxing was continued for another hour. After cooling to room temperature, the solvent was evaporated under reduced pressure. The residue was dissolved in about 50 ml ether and filtered to remove a small amount of insoluble material. The ether solution was washed with water (1×50 ml), with saturated sodium chloride solution (3×50 ml) and then dried over sodium sulfate. The solvent was evaporated affording the title compound as a light-green amorphous solid.

A small amount of this solid was dissolved in ethylene chloride/methanol solution. Addition of acetic acid did not make the solution any darker in color, but upon addition of HgCl₂/pyridine, the solution turned black.

Illustrative of other compounds of the present invention are those of the following formulae:

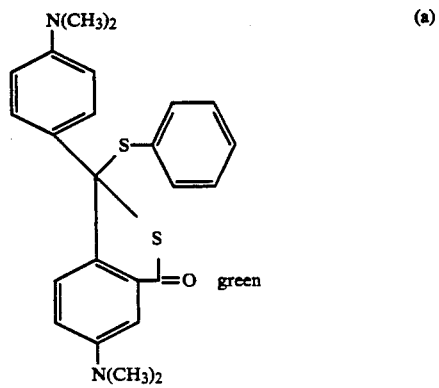
(a) green

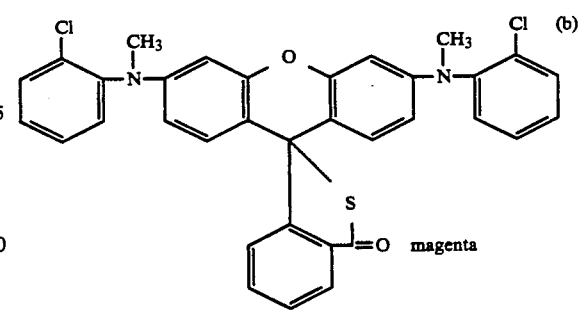
(b) magenta

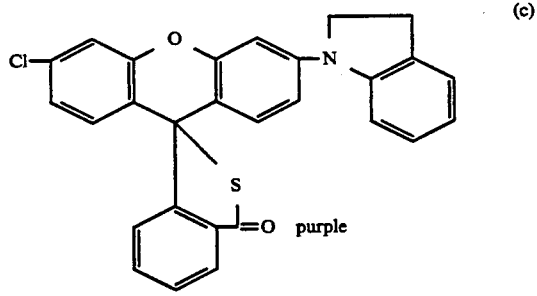
(c) purple

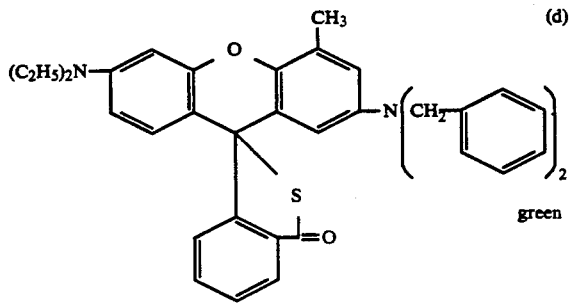
(d) green

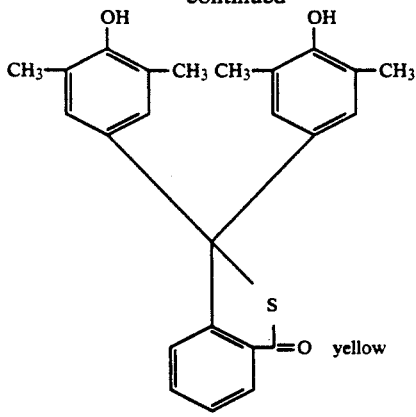

(e)

As mentioned previously, the subject dye precursors exhibit a preference for certain heavy metal ions, particularly silver ion to give the metal complexes of the formulae

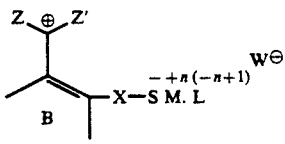

(Ia)

wherein X, B, Z and Z' have the same meaning given above, M is silver, mercury, gold or palladium, L represents a ligand or group of ligands, n is 1, 2, 3 or 4 and W is an anion; and in a preferred embodiment give the following complexes

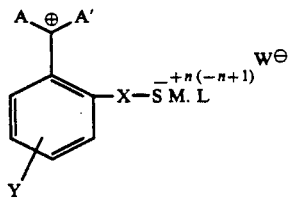

(IIa)

wherein X, Y, A and A', L, M, n and W have the same meaning given above. Preferably, X is

and M is Ag.

The anion W associated with the foregoing compounds may be any suitable single atomic ion or ionic group composed of a plurality of atoms having a negative charge, for example, halide such as chloride, bromide or iodide, nitrate, tetrafluoroborate, perchlorate, periodate, acetate, oxalate, tosylate, sulfate, methane sulfonate, methane hydrogen disulfonate, m-benzene hydrogen disulfonate, trifluoroacetate, hexafluoroacetate, hexafluorophosphorate, azide, trifluoromethane sulfonate, behenate, laurate, and so forth. The ligand L may be any suitable single ion or ionic group having a total negative charge to complete any additional valence of M when n is greater than +1. L may be any of the ions or ionic groups enumerated for W and can include additional molecule(s) of said dye precursor.

To illustrate the specific reactivity to Lewis acid materials versus Bronsted acids, solutions of the thiophthalides of the compounds of the above Examples 1 to 16 were found to be substantially colorless in glacial acetic acid solution but found to colorize to their chromophore color upon the addition of methanolic silver nitrate solution. In comparison, the oxygen analogs, i.e., the corresponding phthalides were colored in acetic acid in the absence of Ag+. Also, when a 0.02 molar solution of the thiophthalide compound of Example 1 and a 0.02 molar solution of a silver uracil complex were mixed at pH 14, the solution was slightly pink. Dropping the pH to about 4 to 5 with acetic acid or with hydrochloric acid generated the chromophore color of the dye by making Ag+ available from the silver uracil complex. In comparison, the addition of acetic acid or hydrochloric acid in the absence of the silver uracil complex did not generate color.

Dithiodichlorofluorane when treated with silver nitrate solution formed a yellow precipitate which rapidly turned brownish yellow. It was determined that the brownish yellow material was a silver sulfide and that the dithiophthalide apparently was converted to the thiophthalide due to the presence of the corresponding thiophthalide in the supernatant solution. It was also noted that the new material did not colorize with silver nitrate.

In a further experiment to determine chromophore color formation with Lewis acids, the thiophthalides of Examples 1 to 12, 14 and 16 and the dithiophthalides corresponding to the thiophthalides of Examples 1, 2, 4 and 9 were placed on silica TLC plates and spot tested with solutions of silver nitrate, mercurous chloride, gold chloride and palladium chloride, respectively. It was found that all of the above-denoted compounds gave their chromophore color with all of these Lewis acids. The thiophthalides of Examples 1 to 6, 9 to 11 and 16 when tested in the same manner with mercuric chloride also gave their chromophore color though only slight color was formed with the thiophthalides of Examples 9 and 11 and also with the dithiophthalide corresponding to the thiophthalide of Example 9. In comparison, when diphenyldithiophthalide was tested in the same manner, it formed brown-orange with palladium and gold, brown-gray with silver and showed no change with mercurous chloride. Dithiodichlorofluorane when tested in the same manner formed yellow with palladium, brown with gold, yellow-gray with silver and showed no change with mercurous chloride.

The thiophthalides of Examples 4, 6 to 12, 14 and 16 and the dithiophthalides corresponding to the thiophthalides of Examples 4 and 9 also were tested with an anhydrous aluminum chloride solution. No color change was observed with the thiophthalides of Examples 4, 6 and 9. The thiophthalides of Examples 7, 8, 10, 12, 14 and 16 gave their chromophore color, though. Examples 7, 12 and 14 gave only slight color as did diphenyldithiophthalide and dithiodichlorofluorane. Aluminum ion added as a salicylate or methoxide complex did not impart color. Presumably due to the formation of a carbonium complex with aluminum rather than a lactone complex, Example 11 gave yellow rather than the blue chromophore color. The dithiophthalide of Example 4 showed no change and the dithiophthalide of Example 9 went colorless which was determined to result from the conversion of the dithiophthalide to the corresponding thiophthalide.

The dithiodichlorofluorane gave slight yellow coloration with boron trifluoride etherate which presumably also was due to the formation of a carbonium ion complex. The thiophthalides of Examples 10 and 16 gave their chromophore color. However, the thiophthalides of Examples 4, 9 and 11 showed no color change and the dithiophthalide corresponding to the thiophthalide of Example 4 also showed no change.

The thiophthalides of Examples 1 to 12, 14 and 16 and the dithiophthalides corresponding to the thiophthalides of Examples 1, 2, 4 and 9 showed no color change on silica TLC plates in the absence of a Lewis acid nor did those compounds exhibit any color change when treated with Bronsted acids, such as, glacial acetic acid and 2,5-diisopropylsalicylic acid. It was found, however, that the phthalides used as the starting materials for the subject thio- and dithiophthalides gave their chromophore color with these Bronsted acids and on silica TLC plates. In contrast, diphenylphthalide and fluoresceinchloride gave no color change on silica or with these Bronsted acids nor did their corresponding dithiophthalides under the same conditions.

As an illustration of the usefulness of these compounds in imaging systems employing inorganic silver salts, the thiophthalide compound of Example 1 and 4-methylphenyl hydroquinone were disposed in a layer on a polyester support under a photosensitive silver halide layer. After imagewise photoexposure, an aqueous processing composition comprising a boric acid/sodium hydroxide buffer containing 3% by weight of benzylaminopurine was applied in a conventional manner in a layer between the exposed photosensitive element and a spreader sheet, and after heating at 75° C for 10 to 20 minutes, a magenta image was formed with gray highlights.

As noted above, in a preferred embodiment, the present invention is concerned with recording materials employing organic silver salts and the above-denoted dye precursors for producing dye images, and preferably employing the thiophthalide dye precursors.

The organic silver salts which can be employed in this invention include silver salts of long chain aliphatic carboxylic acids such as silver laurate, silver myristate, silver palmitate, silver stearate, silver arachidate and silver behenate; silver salts of organic compounds having an imino group such as benzotriazole silver salt, benzimidazole silver salt, carbazole silver salt and phthalazinone silver salt; silver salts of sulfur containing compounds such as S-alkylthioglycollates; silver salts of aromatic carboxylic acids such as silver benzoate and silver phthalate; silver salts of sulfonic acids such as silver ethanesulfonate; silver salt of sulfinic acids such as silver o-toluenesulfinate; silver salts of phosphoric acids such as silver phenylphosphate; silver barbiturate; silver saccharate; silver salts of silicylaldoxime; and any mixtures thereof. Of these compounds, silver salts of long chain aliphatic carboxylic acids are preferred and particularly, silver behenate which may be used in admixture with other organic silver salts if desired. Also, behenic acid may be used with the silver behenate.

The preparation of such organic silver salts is generally carried out by processes which comprise mixing a silver salt forming organic compound dispersed or dissolved in a suitable liquid with an aqueous solution of a silver salt such as silver nitrate or a silver complex salt. Various procedures for preparing the organic silver salts are described in U.S. Pat. Nos. 3,458,544; 4,028,129 and 4,273,723.

Besides the dye precursor and organic silver salt, the image-recording materials preferably include a heat-fusible organic acidic material which upon heating to processing temperatures provides an improved reaction medium for facilitating contacting and reaction of the dye precursor and Ag+ to produce the dye image. The acidic material usually is a phenol or an organic carboxylic acid, particularly a hydroxy-substituted aromatic carboxylic acid. Examples of useful acidic materials include 4,4'-sulfonyldiphenol, Bisphenol A, 5,5'-thiodisalicylic acid, 5-chlorosalicylic acid, salicylic acid, 3,5-diisopropylsalicylic acid, 3-methoxysalicylic acid, mandelic acid, hydroxyacetic acid, 3,4-dihydroxybenzoic acid, 2-hydroxy-3-methyl benzoic acid, 2,5-dihydroxybenzoic acid, 1-hydroxy-2-naphthoic acid, 3-hydroxy-2-naphthoic acid and so forth. It will be appreciated that the particular organic acidic material selected will depend upon the processing temperatures employed and upon the dye precursor and that it may be selected-impirically on the basis of relative performance in giving dye images having the desired maximum and minimum densities for a given image-recording system and the desired image stability.

Where the dye precursor and organic silver salt are contained in separate sheets, the acidic material usually is associated with the organic silver salt. Where the dye precursor and organic silver salt are contained in the same sheet, they may be in the same or different layers on the same or different sides of a support. The heat-fusible organic acidic material may be in the same layer as the dye precursor and/or organic silver salt or in a separate layer. For example, the organic acidic material and organic silver salt may be disposed in one layer and the dye precursor in an adjacent layer or the dye precursor and organic silver salt may be disposed in one layer and the organic acidic material in an adjacent layer. Alternatively, all three components may be contained in the same layer.

Whether in the same or different layers, the dye precursor, organic silver salt and heat-fusible organic acidic material are usually dispersed in a binder which is inert, i.e., does not have any adverse effect on the dye precursor. Also, the binder should be heat-stable at processing temperatures and is preferably transparent so that it does not interfere with viewing of the color image. Besides being inert with respect to the dye precursor, the choice of binder is also governed by the choice of the other components especially the organic silver salt. When the organic silver salt comprises a heterocyclic compound, for example, a triazole, a hydrophilic binder is more suitable such as gelatin, polyvinyl alcohol or hydroxyethylcellulose. When the organic silver salt comprises a long chain aliphatic acid, for example, stearic or behenic acid, a hydrophobic binder is preferred such as polyvinyl butyral, cellulose acetate or ethyl cellulose. If desired, a mixture of binders may be employed.

The layer or layers of the above-mentioned imaging components can be coated on a variety of supports to provide images on one or both sides of the support. Depending upon whether the color image is to be viewed by transmission or reflection, the support may be transparent or opaque. Useful supports are those that retain their dimensional stability at processing temperatures and are resistant to the solvent employed in applying the image-recording layers to the support. Typical supports include paper, paper coated with baryta, polyethylene or other pigment or resin, metal foils and plastic films such as cellulose acetate, polyethylene, polypropylene, polycarbonate and polyethylene terephthalate. Where the dye precursor and organic silver salt are carried on separate supports that are retained together after image formation, at least one of the supports should be transparent to permit viewing of the image. Also, the support should be transparent when images are formed on both sides of the support, e.g., to provide a bichrome or where two or more monochromes are superposed to give a multicolor image.

A method of thermal imaging using these recording materials comprises heating imagewise a recording element which comprises a support carrying at least one layer comprising (a) at least one of said dye precursor compounds having associated therewith in the same or a different layer (b) an organic silver salt and optionally, (c) a heat-fusible organic acidic material, said imagewise heating providing an imagewise distribution of Ag+ for reaction with said dye precursor compound whereby color is formed in an imagewise pattern corresponding to said imagewise heating. The way in which the heat is applied or induced imagewise may be realized in a variety of ways, for example, by direct application of heat using a thermal printing head or thermal recording pen, by conduction from heated image-markings of an original using conventional thermographic copying techniques or by heat generated in response to an electric signal by including, e.g., an electroconductive material or a resistive layer. Also, selective heating may be produced in the image-forming layer(s) by the conversion of electromagnetic radiation into heat. Preferably, the light source is a laser beam emitting source such as a gas laser or semiconductor laser diode.

In the latter embodiment an infra-red absorbing substance is employed for converting infra-red radiation into heat for providing an imagewise distribution of Ag+ for effecting imagewise color formation. Preferably, the infra-red absorber is an organic compound such as a cyanine, merocyanine or thiopyrylium dye and preferably, it is substantially non-absorbing in the visible region of the electromagnetic spectrum so that it will not add any substantial amount of color to the $D_{min}$ areas, i.e., the highlight areas of the dye image.

In the production of multicolor images, infra-red absorbers may be selected that absorb radiation at different predetermined wavelengths above 700 nm as described in U.S. Pat. No. 4,529,992. The wavelengths selected are usually at least about 60 nm apart so that each set of color-forming components may be exposed separately and independently of the others by using infra-red radiation at the particular wavelengths selectively absorbed by the respective infra-red absorbers. As an illustration, the layer(s) containing the components for forming yellow, magenta and cyan may have infra-red absorbers associated therewith that absorb radiation at 760 nm, 820 nm and 1100 nm, respectively, and may be addressed by laser beam sources, for example, infra-red laser diodes emitting laser beams at these respective wavelengths so that the yellow imaging layer can be exposed independently of the magenta and cyan imaging layers, the magenta imaging layer can be exposed independently of the yellow and cyan imaging layers, and the cyan imaging layer can be exposed independently of the yellow and magenta imaging layers. While each set of components may be exposed in a separate scan, it is usually preferred to expose all of them simultaneously in a single scan using multiple laser beam sources of the appropriate wavelengths. Rather than using superimposed imaging layers, the color-forming components and associated infra-red absorbers may be arranged in an array of side-by-side dots or stripes in a single recording layer.

In a further embodiment, multicolor images may be produced using the same infra-red absorbing compound in association with each of two or more sets of color-forming components and exposing each by controlling the depth of focussing of the laser beam. In this embodiment, the concentration of infra-red absorber is adjusted so that each of the infra-red absorbing layers absorb approximately the same amount of laser beam energy. For example, where there are three infra-red absorbing layers, each layer would absorb about one-third of the laser beam energy. It will be appreciated that controlling the focussing depth to address each layer separately may be carried out in combination with the previous embodiment of using infra-red absorbers that selectively absorb at different wavelengths in which instance the concentration of infra-red absorber would not have to be adjusted for the laser beam energy since the first infra-red dye would not absorb any substantial amount of radiation at the absorption peaks of the second and third dyes and so forth.

Where imagewise heating is induced by converting light to heat as described above, the heat-sensitive element comprising the dye precursor/organic silver salt for providing either monochrome or multicolor images may be heated prior to or during imagewise heating. This may be achieved using a heating platen or heated drum or by employing an additional laser beam source for heating the element while it is being exposed imagewise.

As noted above, the dye precursor and organic silver salt may be carried on the same or on separate supports. In the production of multicolor images, they are usually carried on the same support and preferably are contained in the same layer which preferably also includes the organic acidic material. Where electromagnetic radiation using, for example, a laser source is employed to induce imagewise heating as discussed above, the binder used for the imaging layers should transmit the light intended to bring about image formation.

In a further embodiment, a photosensitive material together with a reducing agent may be included with the organic silver salt and dye precursor to provide a photothermographic image-recording material, i.e., an imaging material that is given an imagewise exposure to light to form a latent image and is then heated overall to form the visible color image.

For photothermographic imaging, a photosensitive silver halide or a component capable of forming a photosensitive silver halide is used in catalytic amounts and in catalytic association with the non-photosensitive organic silver salt. The photosensitive silver halide may be formed simultaneously with the preparation of the organic silver salt, or a compound which forms photosensitive silver halide may be reacted with a previously prepared organic silver salt to convert part of the organic silver salt into silver halide. Also, previously prepared silver halides such as silver chloride, silver bromide, silver iodide, silver bromochloride, silver iodobromochloride, etc. may be mixed with an organic silver salt. For photothermographic systems of the post activatable type, the component capable of forming a photosensitive silver halide upon preliminary heating of the photothermographic layer prior to light exposure may be an organic haloamide or a group IV, V or VI metal halide containing an organic component such as phenyl, substituted phenyl or benzyl groups as described in U.S. Pat. No. 4,347,310.

Spectral sensitizing dyes can be used to confer additional sensitivity to the silver halide and to sensitize two or more of the image-recording layers to different specific wavelengths for use in producing multicolor dye images. Spectral sensitizers which can be used include cyanines including trinuclear and tetranuclear cyanines, merocyanines including trinuclear and tetranuclear merocyanines, styryls, oxonols, thiopyrylium and other such dyes as commonly used in the art. The sensitizing dye can be added to the final dispersion of organic silver salt and silver halide or can be added at an earlier stage.

In the photothermographic materials a reducing agent for silver ions also is employed The reducing agents used include organic reducing agents which have a reduction ability suitable for the organic silver salt to form a silver image as a result of the catalytic activity of the silver halide in the exposed area when heated. For example, with an organic silver salt such as silver laurate which is relatively easy to reduce, relatively weak reducing agents are preferably employed On the other hand, with an organic silver salt such as benzotriazole silver salt which is relatively hard to reduce, relatively strong reducing agents are preferably employed. A suitable organic reducing agent or combination thereof may be selected from substituted or unsubstituted bisphenols, substituted or unsubstituted naphthols, mono-, di- or polyhydroxybenzenes, hydroquinone ethers, ascorbic acid or its derivatives, 3-pyrazolidones, pyrazoline-5-ones, aminophenols and p-phenylenediamines. Examples of such reducing agents include 2,2-bis-(4-hydroxyphenyl) propane, 1,1-bis(2-hydroxy-3-t-butyl-5-methylphenyl)methane, 1-naphthol, 1-hydroxy-4-methoxynaphthalene, p-phenylphenol, p-t-butylphenol, catechol, pyrogallol, chlorohydroquinone, 2,5-dimethylhydroquinone, hydroquinone monobenzyl ether, hydroquinone mono-n-hexyl ether, ascorbic acid, ethyl ascorbate, 1-phenyl-3-pyrazolidone, 4-methyl-4-hydroxymethyl-1-phenyl-3-pyrazolidone, 1-phenyl-4-amino-5-pyrazolone, p-aminophenol, 2-methoxy-4-aminophenol and N,N'-diethyl-p-phenylenediamine. Also, reducing agent precursors which, for example, provide a reducing agent upon heating also may be employed. Reducing agents commonly employed with silver behenate because of their light stability and resistance to color change in light include ortho-alkyl- or ortho-aryl-substituted hindered phenols such as 2,6-di-t-butyl-4-methylphenol, 2,2'-methylenebis-(4-ethyl-6-t-butylphenol) and bis (3,5-di-t-butyl-4-hydroxyphenyl) ether. The reducing agent or reducing agent precursor preferably is present in the photosensitive layer comprising the organic silver salt and its associated photosensitive silver halide or photosensitive silver halide-forming component.

In addition to the above-described components, these materials may contain conventional modifiers such as an anti-foggant for heat development, e.g., mercuric acetate; a background-darkening preventive agent, e.g., 1,2,3,4-tetra-bromobutane; a matting agent, e.g., silica; a brightening agent, e.g., a stilbene; a filter/antihalation dye, e.g., 1'-ethoxy-3-ethylthia-2'-cyanine tetrafluoroborate; a toning agent, e.g., phthalazinone; and other addenda which are described, for example, in aforementioned Research Disclosure No. 17029 and which are deemed appropriate for a given image-recording material.

A variety of exposure means are useful for providing a latent image in the photothermographic material. Typically, a latent image is obtained by imagewise exposure to electromagnetic radiation including visible, ultraviolet and infra-red radiation using various light sources such as xenon, tungsten, mercury, iodine or other lamps, lasers, laser diodes, light-emitting diodes and CRT light sources. The exposure should be at least sufficient to provide a developable latent image. Methods for achieving imagewise exposure include photographing with a camera, projective exposure, contact exposure and scanning with a laser beam or other pinpoint source. The use of a laser beam is not only well suited for recording in a scanning mode but by utilizing a highly concentrated beam, photo-energy can be concentrated in a small area so that it is possible to record at high speed and high density. Also, it is a convenient way to record data as a light pattern or a heat pattern in response to transmitted signals such as digitized information and a convenient way of preparing multicolor images by employing a plurality of laser beam sources that emit laser beams of different wavelengths.

After imagewise exposure of the photothermographic material, the dye image can be developed by uniformly heating the photothermographic layer(s) to moderately elevated temperatures for the length of time sufficient to provide the desired dye image. In this embodiment, dye image formation occurs only where development has not taken place, i.e., in areas where Ag+ is still available for reaction with the dye precursor. Preferably, the developed silver is in a low covering power state. Any suitable means can be used as the heating means, for example, a heated platen. a heated drum or roller, or a laser. Also, the material can be passed through a heated atmosphere or heated by high frequency. If desired or appropriate, the photothermographic layer(s) may be heated prior to or during imagewise exposure.

In addition to the layer or layers containing the above-named components, the thermographic and photothermographic image-recording elements may contain additional layers, for example, a subbing layer to improve adhesion to the support, interlayers or barrier layers for thermally and chemically isolating the respective organic silver salt/dye precursor layer(s) from each other, infra-red absorbing layers, antihalation layers, antistatic layers, back coat layers on the support and other auxiliary layers. For use as magnetic tickets such as commuter tickets and passes, a magnetic recording layer may be carried on the back of the support opposite the imaging layer(s), and for use as adhesive labels, an adhesive layer may be coated on the back of the support and a disposable backing sheet attached to the adhesive layer. As mentioned above, an electroconductive layer may be included and imagewise color formation effected by heat energy in response to an electric signal.

Also, a topcoat or overcoat layer is desirable to prevent abrasion and fingerprints, improve shelf life and enhance transparency of the image formed. The overcoat layer may comprise any organic solvent-soluble or water-soluble polymer or resin and preferably contains a fluorochemical surfactant. Also, it may contain ultraviolet absorbers, matting agents, higher fatty acids, waxes and other materials as commonly employed in such layers. Suitable polymers for the overcoat layer include polyvinyl chloride, polyvinyl acetate, copolymers of vinyl chloride and vinyl acetate, polyvinyl butyral, polystyrene, poly-methyl methacryalate, polyurethane, xylene resins, benzyl cellulose ethyl cellulose, cellulose acetate butyrate, cellulose acetate, cellulose triacetate, polyvinylidene chloride, chlorinated polypropylene, polyvinylpyrrolidone, cellulose propionate, polyvinyl formal, cellulose acetate phthalate, polycarbonate and cellulose acetate propionate, etc. Preferred topcoat layers comprise chrome-hardened polyvinyl alcohol, methacrylic acid-diacrylamide copolymers and arylsulfonamideformaldehyde condensation resins containing a fluorocarbon surfactant.

The thermographic and photothermographic composition layer(s) and other layers may be coated on a suitable support by various coating procedures including dip coating, air-knife coating, roll coating, curtain. coating and extrusion coating. If desired, two or more layers can be coated simultaneously. The coating compositions may contain dispersing agents, surfactants, lubricants, plasticizers, defoaming agents, coating aids, pigments, e.g., to provide a white background or a contrasting color for the dye image formed, and so forth. The layers may then be dried at ambient or elevated temperatures provided the temperature is not sufficient to effect premature color formation.

In the elements used for producing both monochrome and multicolor images, the dye precursors are selected to give the desired color including "black" or the desired combination of colors, and for multicolor images, the dye precursors generally are selected to give the subtractive colors cyan, magenta and yellow as commonly employed in conventional photographic processes to provide full natural color.

The following examples are given to further illustrate the present invention but are not intended to limit the scope thereof.

EXAMPLES I-V

A silver behenate full soap was prepared using the following:

| | | |
|---|---|---|
| 3 | liters | Distilled water |
| 120 | grams | Behenic acid (0.35 mole) |
| 14.1 | grams | Sodium hydroxide in 100 ml water (0.35 mole) |
| 1 | ml | Conc. nitric acid in 10 ml water (20.01 mole) |
| 59.25 | grams | Silver nitrate in 200 ml water (0.35 mole) |

The distilled water was placed in a 5 liter round bottom flask filtered with a Hirschberg stirrer and a heating mantle. After bringing the temperature of the distilled water up to about 80° C., the behenic acid was added and the resulting mixture was stirred vigorously until it became finely dispersed (approximately 20 minutes). The sodium hydroxide was added dropwise at a rapid rate using an addition funnel. The reaction mixture at about 80° C. was then stirred for another one-half hour until a milky colloid was formed. The nitric acid was then added to the dispersion to ensure that no free hydroxide remained. Heating was discontinued and the temperature was reduced to about 50° C. at which time the silver nitrate was added dropwise to the dispersion over a one-half hour period with vigorous stirring. Stirring was continued until a noticeable reduction in the viscosity (thinning of the dispersion) occurred and then the dispersion was stirred for an additional 20 minutes to ensure that all reactants had been consumed.

The silver behenate was recovered from the dispersion by filtration using a Buckner funnel, slurried in 2 liters of distilled water, filtered, washed with distilled water in the Buckner funnel until no silver chloride was formed in the filtrate upon addition of sodium chloride and then dried for several days at 50° C. to a constant weight.

A polymer dispersion containing 5.5% by weight of silver as silver behenate was obtained by ball-milling the following for 48 hours:

100 grams of dry silver behenate as prepared above in 220 grams of methyl ethyl ketone, 60 grams of toluene and 50 grams methyl isobutyl ketone with 10 grams of polyvinylbutyral ("Butvar B-76").

This silver behenate dispersion was employed in the following compositions A through E which were used to prepare a series of image-recording elements. The image-recording elements were fabricated by applying a layer of composition to a transparent polyethylene terephthalate support using a No. 38 Mayer rod and then allowing the coated layer to dry at room temperature. Composition A:

| Composition A: | |
|---|---|
| 35 mg | Compound of Example 8 |
| 42 mg | 4,4'-Sulfonyldiphenol |
| 81 mg | Polyvinylbutyral (10% in acetone) |
| 2.0 g | Acetone |
| 175 mg | Silver behenate dispersion |
| Composition B: | |
| 23 mg | Compound of Example 3 |
| 23 mg | 3,5-Diisopropylsalicylic acid |
| 54 mg | Polyvinylbutyral (10% in acetone) |
| 1.35 g | Acetone |
| 115 mg | Silver behenate dispersion |
| Composition C: | |
| 23 mg | Compound of Example 4 |
| 23 mg | 3,5-Diisopropylsalicylic acid |
| 54 mg | Polyvinylbutyral (10% in acetone) |
| 1.35 g | Acetone |
| 115 mg | Silver behenate dispersion |
| Composition D: | |
| 23 mg | Compound of Example 9 |
| 23 mg | 3,5-Diisopropylsalicylic acid |
| 80 mg | Polyvinylbutyral (10% in acetone) |
| 2.1 g | Acetone |
| 130 mg | Silver behenate dispersion |
| Composition E: | |
| 23 mg | Compound of Example 10 |
| 23 mg | 4,4'-Sulfonyldiphenol |
| 54 mg | Polyvinylbutyral (10% in acetone) |
| 2.35 g | Methyl ethyl ketone |
| 115 mg | Silver behenate dispersion |

A portion of each image-recording element was heated by contacting with a hot plate at 110° C. for about 15 to 20 seconds. Then the maximum and minimum transmission densities were measured for the heated and unheated portion of the elements using a Macbeth transmission densitometer Model TD504 equipped with an S4 photomultiplier and color Filter Nos. 29, 93 and 94 for red (R), green (G), and blue (B), respectively. The results are reported in the following Table.

TABLE

| Example | $D_{max}/D_{min}$ |
|---|---|
| I | 0.11/0.02(R) |
| | 1.27/0.03(G) |
| | 0.44/0.03(B) |
| II | 0.059/0.03(R) |
| | 0.64/0.04(G) |

TABLE-continued

| Example | $D_{max}/D_{min}$ |
|---|---|
| | 0.66/0.05(B) |
| III | 0.12/0.03(R) |
| | 0.49/0.06(G) |
| | 0.96/0.05(B) |
| IV | 2.02/0.04(R) |
| | 1.13/0.03(G) |
| | 0.25/0.04(B) |
| V | 0.22/0.02(R) |
| | 1.48/0.04(G) |
| | 0.43/0.04(B) |

A silver behenate dispersion as prepared above was employed in the following Examples.

EXAMPLE VI

An image-recording element was prepared by coating the following layers out of a solution comprising methyl ethyl ketone on a transparent polyethylene terephthalate support
(1) a layer comprising the Compound of Example 10 coated at a coverage of 75 mgs/ft$^2$, silver behenate coated at a coverage of 23 mgs/ft$^2$ of silver and polyvinylbutyral coated at a coverage of 125 mgs/ft$^2$;
(2) a layer comprising 4,4'-sulfonyldiphenol coated at a coverage of 90 mgs/ft$^2$ and polyvinylbutyral coated at a coverage of 100 mgs/ft$^2$ and
(3) a topcoat layer of cellulose acetate coated at a coverage of 100 mgs/ft$^2$.

The image-recording element (coated surface) was placed against the printed surface of an original to be copied and then imaged using a thermographic office copier to give a transparency having a magenta image. The high intensity radiation provided by the thermographic copier is preferentially absorbed by the infrared absorbing characters of the original, and the absorbed radiation is converted to heat which melts the silver behenate to provide Ag+ for reaction with the thiophthalide compound whereby a magenta image is formed in the image-recording element corresponding to the printed pattern of the original. The maximum and minimum transmission densities measured for the imaged element were 0.25/0.02 (R), 2.15/0.03 (G) and 0.52/0.04 (B).

EXAMPLE VII

An image-recording element was prepared by coating the following layers out of a solution comprising methyl ethyl ketone on a transparent polyethylene terephthalate support:
(1) a layer comprising the Compound of Example 9 coated at a coverage of 50 mgs/ft$^2$, silver behenate coated at a coverage of 12 mgs/ft$^2$ of silver, polyvinylbutyral coated at a coverage of 125 mgs/ft$^2$, and 1,4-butanediol diglycidyl ether coated at a coverage of 6.25 mgs/ft$^2$;
(2) a layer comprising 3,5-diisopropylsalicylic acid coated at a coverage of 50 mgs/ft$^2$, polyvinylbutyral coated at a coverage of 100 mgs/ft$^2$ and 1,4-butanediol diglycidyl ether coated at a coverage of 5 mgs/ft$^2$; and
(3) a topcoat layer of cellulose acetate coated at a coverage of 100 mgs/ft$^2$.

This image-recording element was superposed with an original and imaged using a thermographic office copier in the same manner described in Example VI to give a transparency having a blue image. The maximum and minimum transmission densities measured for the imaged element were 1.6/0.03 (R), 0.78/0.04 (G) and 0.2/0.04 (B).

EXAMPLE VIII

An image-recording element was prepared by coating the following layers on a transparent polyethylene terephthalate support:
(1) a layer comprising 3,5-diisopropylsalicylic acid coated at a coverage of 50 mgs/ft$^2$, silver behenate coated at a coverage of 12 mgs/ft$^2$ silver, polyvinylbutyral coated at a coverage of 125 mgs/ft$^2$ and 1,4-butanediol diglycidyl ether coated at a coverage of 6.25 mgs/ft$^2$;
(2) a layer comprising the Compound of Example 9 coated at a coverage of 50 mgs/ft$^2$, polyvinylbutyral coated at a coverage of 100 mgs/ft$^2$ and 1,4-butanediol coated at a coverage of 5 mgs/ft$^2$; and
(3) a topcoat layer of cellulose acetate coated at a coverage of 100 mgs/ft$^2$.

This image-recording element was imaged in the same manner described in Example VI to give a transparency containing a blue image. The maximum and minimum transmission densities measured for the imaged element were 1.93/0.02 (R), 0.86/0.03 (G) and 0.19/0.04 (B).

To illustrate the add-on capability of the subject recording materials, this recording element was imaged ten times to successively extend a line and it was found that the added portions could be made without any deleterious effect on the previous portions.

EXAMPLE IX

An image-recording element was prepared by coating the following layers on a transparent polyethylene terephthalate support:
(1) a layer comprising 4,4'-sulfonyldiphenol coated at a coverage of 75 mgs/ft$^2$, silver behenate coated at a coverage of 25 mgs/ft$^2$ silver, polyvinylbutyral coated at a coverage of 250 mgs/ft$^2$ and 1,4-butanediol diglycidyl ether coated at a coverage of 12 mgs/ft$^2$;
(2) a layer comprising the Compound of Example 10 coated at a coverage of 75 mgs/ft$^2$, polyvinylbutyral coated at a coverage of 125 mgs/ft$^2$ and 1,4-butanediol ether coated at a coverage of 6.25 mgs/ft$^2$; and
(3) a topcoat layer of cellulose acetate coated at a coverage of 100 mgs/ft$^2$.

This image-recording element was imaged in the same manner described in Example VI to give a transparency having a magenta image. The maximum and minimum densities measured for the imaged element were 0.21/0.03 (R), 1.60/0.03 (G) and 0.39/0.04 (B).

EXAMPLE X

An image-recording element was prepared by coating the following layers on a transparent polyethylene terephthalate support:
(1) a layer comprising 3,5-diisopropylsalicylic acid coated at a coverage of 160 mgs/ft$^2$, silver behenate coated at a coverage of 40 mgs/ft$^2$ silver, polyvinylbutyral coated at a coverage of 400 mgs/ft$^2$ and 1,4-butanediol diglycidyl ether coated at a coverage of 20 mgs/ft$^2$;
(2) a layer comprising the Compound of Example 7 coated at a coverage of 80.5 mgs/ft$^2$, polyvinylbutyral coated at a coverage of 200 mgs/ft² and 1,4-butanediol diglycidyl ether coated at a coverage of 10 mgs/ft²; and (3) a topcoat layer of cellulose acetate coated at a coverage of 100 mgs/ft².

This image-recording element was imaged in the same manner described in Example VI to give a green image. The maximum and minimum transmission densities measured for the imaged element were 2.05/0.03 (R), 0.37/0.03 (G) and 0.65/0.04 (B).

EXAMPLE XI

An image-recording element was prepared by coating a transparent polyethylene terephthalate support with the following layers:

(1) a layer comprising silver behenate coated at a coverage of 60 mgs/ft² silver, 4,4'-sulfonyldiphenol coated at a coverage of 172.5 mgs/ft², polyvinylbutyral coated at a coverage of 375 mgs/ft² and 1,4-butanediol diglycidyl ether coated at a coverage of 18 mgs/ft²;

(2) a layer comprising the Compound of Example 3 coated at a coverage of 172.5 mgs/ft², the Compound of Example 10 coated at a coverage of 19.5 mgs/ft², polyvinylbutyral coated at a coverage of 187.5 mgs/ft² and 1,4-butanediol diglycidyl ether coated at a coverage of 9.3 mgs/ft²; and (3) a topcoat layer of cellulose acetate coated at a coverage of 100 mgs/ft².

This image-recording element was imaged in the same manner described in Example VI to give a transparency having a black image. The maximum and minimum transmission densities measured for the imaged element were 1.80/0.03 (R), 1.86/0.03 (G) and 2.04/0.04 (B).

EXAMPLE XII

An image-recording element was prepared by coating a transparent polyethylene terephthalate support with the following layers:

(1) a layer comprising silver behenate coated at a coverage of 12 mgs/ft² silver, polyvinylbutyral coated at a coverage of 250 mgs/ft² and 3,5-diisopropylsalicylic acid coated at a coverage of 50 mgs/ft²;

(2) a layer comprising the compound of Example 9 coated at a coverage of 50 mgs/ft² and polyvinylbutyral coated at a coverage of 100 mgs/ft²; and (3) a topcoat layer comprising polyvinylalcohol coated at a coverage of 30 mgs/ft²; Quilon C available from the duPont Company (chromium, pentahydroxy tetradecanato)di-) coated at a coverage of 30 mgs/ft² and Fluorad FC-100 available from the 3M Company (fluorochemical surfactant-fluorinated alkyl amphoteric mixture) coated at a coverage of 15 mgs/ft².

This image-recording element was imaged in the same manner described in Example VI to give a blue image. The maximum and minimum transmission densities measured for the imaged element were 1.96/0.02 (R), 0.84/0.03 (G) and 0.18/0.04 (B).

EXAMPLE XIII

An image-recording element was prepared by coating the following layers on a transparent polyethylene terephthalate support;

(1) a layer comprising the Compound of Example 1 coated at a coverage of 50 mgs/ft², silver behenate coated at a coverage of 15 mgs/ft² silver and polyvinylbutyral coated at a coverage of 50 mgs/ft² and (2) a topcoat layer of polyvinylbutyral coated at a coverage of about 100 mgs/ft.

This image-recording element was imaged in the same manner described in Example VI to give a magenta image. The maximum and minimum transmission densities measured for the imaged element were 0.10/0.04 (R), 1.31/0.05 (G) and 0.18/0.05 (B).

EXAMPLE XIV

An image-recording element was prepared by coating a transparent polyethylene terephthalate support with a layer comprising the compound of Example 26 coated at a coverage of 50 mgs/ft², silver behenate coated at a coverage of 12 mgs/ft² silver and polyvinylbutyral coated at a coverage of 120 mgs/ft².

The element was imaged in the same manner described in Example VI to give a magenta image. The maximum and minimum transmission densities measured for the imaged element were 0.05/0.03 (R), 1.85/0.22 (G) and 0.17/0.05 (B).

EXAMPLE XV

An image-recording element was prepared by coating the following layers on the reverse side of Example XII:

(1) a layer comprising silver behenate coated at a coverage of 23 mgs/ft² silver, polyvinylbutyral coated at a coverage of 300 mgs/ft² and 3,5-diisopropylsalicylic acid coated at a coverage of 60 mgs/ft²;

(2) a layer comprising the compound of Example 8 coated at a coverage of 63 mgs/ft² and polyvinylbutyral coated at a coverage of 56 mgs/ft²; and (3) a topcoat layer identical to topcoat layer (3) of Example XII.

This image-recording element was imaged with a thermographic office copier against a xerographic original to give a blue image when processed against one side and a red image when processed against the opposite side. The maximum and minimum transmission densities measured for the imaged element were:

Blue image: 1.96/0.02 (R), 0.84/0.03 (G) and 0.18/0.04 (B)
Red image: 0.14/0.03 (R), 1.20/0.04 (G) and 0.60/0.04 (B)

EXAMPLE XVI

A recording element was prepared by coating a transparent support with a layer comprising the compound of Example 10 coated at a coverage of 75 mgs/ft², silver behenate coated at a coverage of 25 mgs/ft² silver, 4,4'-sulfonyldiphenol coated at a coverage of 75 mgs/ft², polyvinylbutyral coated at a coverage of 120 mgs/ft² and an infrared absorber having the formula

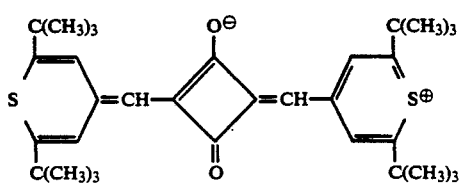

coated at a coverage of 5.5 mgs/ft².

The coated sample was irradiated through the transparent support using a laser diode emitting at a wavelength of 810 nm and at an output of 27 m Watts at the film plane at a scanning rate of 0.5 microns per microsecond to give a fully colored magenta 25 micron×5 micron track.

Since certain changes may be made in the herein described subject matter without departing from the scope of the invention herein involved, it is intended that all matter contained in the above description and examples be interpreted as illustrative and not in a limiting sense.

What is claimed is:

1. A recording material which comprises (a) at least one di- or triarylmethane dye precursor compound

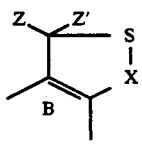

wherein X is

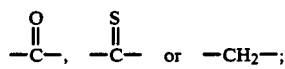

ring B represents a substituted or unsubstituted carbocyclic aryl ring or a heterocyclic aryl ring; and Z and Z' taken individually represent the moieties to complete the auxochromophoric system of a diarylmethane or a triarylmethane dye when said S-containing ring is open and Z and Z' when taken together represent the bridged moieties to complete the auxochromophoric system of a bridged triarylmethane dye when said S-containing ring is open, and (b) a Lewis acid material capable of opening said S-containing ring whereby said compound is rendered colored, said dye precursor compound being coated on a support and said Lewis acid material being coated on the same or on a separate support.

2. A recording material as defined in claim 1 wherein said X is

3. A recording material as defined in claim 1 wherein Y is

4. A recording material as defined in claim 1 wherein X is —CH₂—.

5. A recording material as defined in claim 1 wherein said (a) dye precursor compound and said (b) Lewis acid material are coated on the same support.

6. A recording material as defined in claim 5 wherein said (b) Lewis acid material is a silver salt.

7. A recording material as defined in claim 6 wherein said recording material comprises a support carrying at least one layer comprising (a) at least one dye precursor compound having associated therewith in the same or a different layer (b) an organic silver salt and optionally, (c) a heat-fusible organic acidic material.

8. A recording material as defined in claim 7 wherein said recording material comprises a transparent support carrying on each side thereof at least one said layer of said dye precursor compound and its associated organic silver salt.

9. A recording material as defined in claim 7 which additionally includes a catalytic amount of (a) a photosensitive silver halide or a component capable of forming a photosensitive silver halide in association with (b) said organic silver salt and with (c) an organic reducing agent.

10. A recording material as defined in claim 7 which additionally includes a binder.

11. A recording material as defined in claim 10 wherein said binder is polyvinylbutyral.

12. A recording material as defined in claim 10 wherein said organic silver salt is silver behenate.

13. A recording material as defined in claim 10 wherein said heat-fusible organic acidic material is a phenol.

14. A recording material as defined in claim 10 wherein said heat-fusible organic acidic material is an organic carboxylic acid.

15. A recording material as defined in claim 10 which includes an infrared absorbing substance associated with each said layer of dye precursor compound and its associated organic silver salt.

16. A recording material as defined in claim 10 which comprises at least two said layers of said dye precursor compound and associated organic silver salt.

17. A recording material as defined in claim 16 which additionally includes a thermal isolation layer between adjacent said layers of said dye precursor compound and associated organic silver salt.

18. A recording material as defined in claim 16 wherein an infra-red absorber for absorbing radiation at wavelengths above 700 nm is associated with each said layer of dye precursor compound and its associated organic silver salt.

19. A recording material as defined in claim 18 wherein each of said infra-red absorbers absorb radiation at different predetermined wavelengths above 700 nm.

20. A recording material as defined in claim 18 wherein said infra-red absorbers absorb radiation at the same wavelength above 700 nm.

21. A recording material as defined in claim 18 which comprises three said layers of dye precursor compound and associated organic silver salt for forming a cyan image, a magenta image and a yellow image, respectively.

22. A recording material as defined in claim 21 which additionally includes thermal isolation layers between adjacent said layers of said dye precursor compound.

23. A recording material as defined in claim 10 wherein said recording material additionally includes a protective topcoat layer.

24. A recording material as defined in claim 1 wherein said Z and Z' are taken together and represent said bridged moieties.

25. A recording material as defined in claim 24 wherein said ring B represents said carbocyclic aryl ring.

26. A recording material as defined in claim 25 wherein said carbocyclic aryl ring is a benzene ring.

27. A method of forming color which comprises contacting (a) a di- or triarylmethane dye precursor compound having the formula

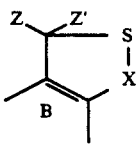

wherein X is

ring B represents a substituted or unsubstituted carbocyclic aryl ring or a heterocyclic aryl ring; and Z and Z' taken individually represent the moieties to complete the auxochromophoric system of a diarylmethane or a triarylmethane dye when said S-containing ring is open and Z and Z' when taken together represent the bridged moieties to complete the auxochromophoric system of a bridged triarylmethane dye when said S-containing ring is open, with (b) a Lewis acid material capable of opening said S-containing ring whereby said compound is rendered colored.

28. A method of forming color as defined in claim 27 wherein said dye precursor compound is triarylmethane compound.

29. A method of forming color as defined in claim 27 wherein X is

30. A method of forming color as defined in claim 27 wherein X is

31. A method of forming color as defined in claim 27 wherein X is —CH$_2$—.

32. A method of forming color as defined in claim 27 wherein said Lewis acid material is a heavy metal ion.

33. A method of forming color as defined in claim 32 wherein said metal ion is mercury.

34. A method of forming color as defined in claim 32 wherein said metal ion is gold.

35. A method of forming color as defined in claim 32 wherein said metal ion is palladium.

36. A method of forming color as defined in claim 32 wherein said metal ion is silver.

37. A method of forming color as defined in claim 27 wherein color is formed imagewise by effecting said contact imagewise.

38. A method of thermal imaging which comprises heating imagewise a recording element which comprises a support carrying at least one layer comprising (a) at least one di- or triarylmethane dye precursor compound having associated therewith in the same or a different layer, (b) an organic silver salt and optionally, (c) a heat-fusible organic acidic material, said dye precursor compound having the formula

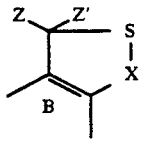

wherein X is

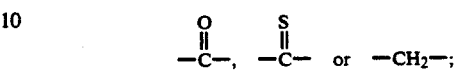

ring B represents a substituted or unsubstituted carbocyclic aryl ring or a heterocyclic aryl ring; and Z and Z' taken individually represent the moieties to complete the auxochromophoric system of a diarylmethane or a triarylmethane dye when said S-containing ring is open and Z and Z' when taken together represent the bridged moieties to complete the auxochromophoric system of a bridged triarylmethane dye when said S-containing ring is open, said imagewise heating providing an imagewise distribution of Ag+ for reaction with said dye precursor compound whereby color is formed in an imagewise pattern corresponding to said imagewise heating.

39. A method of thermal imaging as defined in claim 38 wherein an infra-red absorber for absorbing radiation at wavelengths above 700 nm is associated with each said layer of dye precursor compound at its associated organic silver salt and converting said absorbed radiation into heat for providing said imagewise distribution of Ag+.

40. A method of thermal imaging as defined in claim 39 wherein said imagewise heating is effected by imagewise exposure to a laser beam source emitting infra-red radiation at a wavelength strongly absorbed by said infra-red absorber.

41. A method of thermal imaging as defined in claim 38 wherein said recording element comprises at least two said layers of dye precursor compound and associated organic silver salt.

42. A method of thermal imaging as defined in claim 41 wherein said recording element additionally includes a thermal isolation layer between adjacent said layers of said dye precursor compound and associated organic silver salt.

43. A method of thermal imaging as defined in claim 41 wherein an infra-red absorber for absorbing radiation at wavelengths above 700 nm is associated with each said layer of dye precursor compound and its associated organic silver salt and converting said absorbed radiation into heat for providing said imagewise distribution of Ag+, said infra-red absorbers associated with said layers selectively absorbing radiation at different predetermined wavelengths above 700 nm, said imagewise heating being effected by imagewise exposure to a plurality of laser beam sources emitting infra-red radiation at the respective wavelengths selectively absorbed by said infra-red absorbers.

44. A method of thermal imaging as defined in claim 41 wherein an infra-red absorber for absorbing infra-red radiation at wavelengths above 700 nm is associated with each said layer of dye precursor compound and associated organic silver salt and converting said absorbed radiation into heat for providing said imagewise distribution of Ag+, said infra-red absorbers associated with said layers absorbing infra-red radiation at the same wavelength or at different wavelengths above 700 nm, said imagewise heating being effected by adjusting the depth of focus of a laser beam source emitting radiation at the wavelength absorbed by said infra-red absorbers.

45. A method of thermal imaging as defined in claim 41 wherein said recording element comprises three said layers of dye precursor compound and associated silver salt for forming a cyan image, a magenta image and a yellow image, respectively.

* * * * *